(12) United States Patent
Arinzeh

(10) Patent No.: US 9,181,636 B2
(45) Date of Patent: Nov. 10, 2015

(54) ELECTROSPUN CERAMIC-POLYMER COMPOSITE AS A SCAFFOLD FOR TISSUE REPAIR

(75) Inventor: Treena Lynne Arinzeh, West Orange, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 92 days.

(21) Appl. No.: 13/210,806

(22) Filed: Aug. 16, 2011

(65) Prior Publication Data

US 2011/0300626 A1    Dec. 8, 2011

Related U.S. Application Data

(62) Division of application No. 12/141,340, filed on Jun. 18, 2008.

(60) Provisional application No. 60/944,587, filed on Jun. 18, 2007.

(51) Int. Cl.
| | |
|---|---|
| *C12N 5/077* | (2010.01) |
| *B29C 47/00* | (2006.01) |
| *D01D 5/00* | (2006.01) |
| *A61F 2/28* | (2006.01) |
| *A61L 27/38* | (2006.01) |
| *A61L 27/46* | (2006.01) |
| *D01F 1/10* | (2006.01) |
| *A61F 2/30* | (2006.01) |
| *A61F 2/44* | (2006.01) |

(52) U.S. Cl.
CPC ............... *D01D 5/0007* (2013.01); *A61F 2/28* (2013.01); *A61L 27/3821* (2013.01); *A61L 27/3834* (2013.01); *A61L 27/3847* (2013.01); *A61L 27/46* (2013.01); *D01F 1/10* (2013.01); *A61F 2/3094* (2013.01); *A61F 2002/4495* (2013.01); *A61F 2240/001* (2013.01); *A61F 2310/00179* (2013.01)

(58) Field of Classification Search
CPC . A61F 2/28; A61F 2/3094; A61F 2002/4495; A61F 2240/001; D01F 1/10; A61L 27/3834; A61L 27/3847; A61L 27/46; A61L 27/3821; D01D 5/0007

See application file for complete search history.

(56) References Cited

U.S. PATENT DOCUMENTS

| | | | |
|---|---|---|---|
| 4,846,835 | A | 7/1989 | Grande |
| 5,030,225 | A | 7/1991 | Aebischer et al. |
| 5,250,843 | A | 10/1993 | Eichelberger |
| 5,353,498 | A | 10/1994 | Eillion |
| 5,486,359 | A | 1/1996 | Caplan |
| 5,522,879 | A | 6/1996 | Scopelianos |
| 5,626,861 | A | 5/1997 | Laurencin et al. |
| 5,666,467 | A | 9/1997 | Colak |
| 5,681,873 | A | 10/1997 | Norton et al. |
| 5,766,618 | A | 6/1998 | Laurencin et al. |
| 5,811,094 | A | 9/1998 | Caplan |
| 5,827,735 | A | 10/1998 | Young |
| 5,841,193 | A | 11/1998 | Eichelberger |
| 5,906,934 | A | 5/1999 | Grande et al. |
| 5,955,529 | A | 9/1999 | Imai et al. |
| 6,095,148 | A | 8/2000 | Shastri et al. |
| 6,165,486 | A | 12/2000 | Marra et al. |
| 6,174,333 | B1 | 1/2001 | Kadiyala |
| 6,214,369 | B1 | 4/2001 | Grande et al. |
| 6,306,424 | B1 | 10/2001 | Vyakarnam et al. |
| 6,355,239 | B1 | 3/2002 | Bruder |
| 6,387,367 | B1 | 5/2002 | David-Sproul |
| 6,464,983 | B1 | 10/2002 | Grotendorst |
| 6,472,210 | B1 | 10/2002 | Holy et al. |
| 6,482,231 | B1 | 11/2002 | Abatangelo |
| 6,489,165 | B2 | 12/2002 | Bhatnagar et al. |
| 6,511,511 | B1 | 1/2003 | Slivka et al. |
| 6,541,024 | B1 | 4/2003 | Kadiyala |
| 6,685,956 | B2 | 2/2004 | Chu |
| 6,689,166 | B2 | 2/2004 | Laurencin et al. |
| 6,689,374 | B2 | 2/2004 | Chu et al. |
| 6,730,252 | B1 * | 5/2004 | Teoh et al. ................. 264/178 F |
| 6,783,712 | B2 | 8/2004 | Slivka et al. |
| 6,790,455 | B2 | 9/2004 | Chu |
| 6,790,528 | B2 | 9/2004 | Wendorff et al. |
| 6,863,900 | B2 | 3/2005 | Kadiyala |
| 7,012,106 | B2 | 3/2006 | Yuan et al. |
| 7,022,522 | B2 | 4/2006 | Guan et al. |
| 7,247,313 | B2 | 7/2007 | Roorda et al. |
| 7,271,234 | B2 | 9/2007 | Kohn et al. |

(Continued)

FOREIGN PATENT DOCUMENTS

| | | |
|---|---|---|
| WO | WO 2006/068809 | 6/2006 |
| WO | WO 2006/095021 A1 | 9/2006 |
| WO | WO 2006/106506 | 10/2006 |
| WO | WO 2006106506 A2 * | 10/2006 |
| WO | WO 2008/055038 A2 | 5/2008 |
| WO | WO 2008/157594 | 12/2008 |
| WO | WO 2013/023064 | 2/2013 |

OTHER PUBLICATIONS

Arinzeh, Biomaterials, 26, 2005.*

(Continued)

*Primary Examiner* — Susan Tran
*Assistant Examiner* — William Craigo
(74) *Attorney, Agent, or Firm* — McCarter & English, LLP

(57) ABSTRACT

The present invention relates to compositions and methods of preparing a three-dimensional matrix of micron sized electrospun fibers, wherein the electrospun fibers are formed from a electrospun composite comprising a bioactive ceramic component and a polymer component. The matrix provides an osteoconductive and osteoinductive scaffold supporting osteogenesis and thereby facilitates bone repair.

12 Claims, 13 Drawing Sheets

(56) References Cited

U.S. PATENT DOCUMENTS

| | | | |
|---|---|---|---|
| 7,601,525 | B2 | 10/2009 | Batich et al. |
| 7,619,901 | B2 | 11/2009 | Eichelberger et al. |
| 7,767,221 | B2 | 8/2010 | Lu et al. |
| 7,803,574 | B2 | 9/2010 | Desai |
| 2002/0004039 | A1 | 1/2002 | Reid et al. |
| 2002/0034796 | A1 | 3/2002 | Shastri et al. |
| 2002/0173213 | A1 | 11/2002 | Chu et al. |
| 2003/0054035 | A1 | 3/2003 | Chu et al. |
| 2003/0069369 | A1 | 4/2003 | Belenkaya et al. |
| 2003/0077311 | A1 | 4/2003 | Vyakarnam et al. |
| 2003/0211130 | A1 | 11/2003 | Sanders et al. |
| 2004/0018226 | A1 | 1/2004 | Wnek et al. |
| 2005/0095695 | A1* | 5/2005 | Shindler et al. ............ 435/285.1 |
| 2005/0196423 | A1 | 9/2005 | Batich et al. |
| 2006/0057377 | A1 | 3/2006 | Harrison et al. |
| 2006/0094320 | A1 | 5/2006 | Chen et al. |
| 2006/0128012 | A1* | 6/2006 | Arinzeh et al. ............... 435/366 |
| 2006/0198865 | A1 | 9/2006 | Freyman et al. |
| 2006/0204539 | A1 | 9/2006 | Atala et al. |
| 2006/0240064 | A9 | 10/2006 | Hunter et al. |
| 2007/0179594 | A1 | 8/2007 | Llanos et al. |
| 2007/0267725 | A1 | 11/2007 | Lee et al. |
| 2008/0009599 | A1 | 1/2008 | East et al. |
| 2008/0112150 | A1 | 5/2008 | Jones |
| 2008/0206343 | A1 | 8/2008 | Edinger et al. |
| 2008/0246126 | A1 | 10/2008 | Bowles et al. |
| 2009/0028921 | A1 | 1/2009 | Arinzeh et al. |
| 2009/0048358 | A1 | 2/2009 | Kim |
| 2009/0325296 | A1 | 12/2009 | Arinzeh et al. |
| 2010/0078771 | A1 | 4/2010 | Barth et al. |
| 2010/0078776 | A1 | 4/2010 | Barth et al. |
| 2010/0173158 | A1 | 7/2010 | Furuzono et al. |
| 2010/0233234 | A1 | 9/2010 | Arinzeh et al. |
| 2010/0233807 | A1 | 9/2010 | Arinzeh et al. |
| 2010/0274742 | A1 | 10/2010 | Hodjat et al. |
| 2010/0324697 | A1 | 12/2010 | Arinzeh et al. |
| 2011/0300626 | A1 | 12/2011 | Arinzeh |
| 2013/0052254 | A1 | 2/2013 | Arinzeh et al. |

OTHER PUBLICATIONS

Wutticharoenmongol_Macromolecular Bioscience_vol. 6_Dec. 22, 2005.*

Li, et al., Electrospun Nanofibrous Structure: A Novel Scaffold for Tissue Engineering, Journal of Biomedical Mat. Res., vol. 60, Issue 4, pp. 613-621, 2002.

Li, et al., Biological Response of Chondrocytes Cultured in Three-Dimensional Nanofibrous Poly($\epsilon$ caprolactone) Scaffolds, J. Biomed. Mat. Res. Part A., 67A, 4, pp. 1105-1114, 2003.

Yoshimoto et al., A Biodegradable Nanofiber Scaffold by Electrospinning and its Potential for Bone Tissue Engineering, Biomaterials, 24, pp. 2077-2082, 2003.

Shin et al., In Vivo Bone Tissue Engineering Using Mesenchymal Stem Cells on a Novel Electrospun Nanofibrous Scaffold, Tissue Engineering, 10, pp. 33-41, 2004.

Li et al., Carbon Nanotubes Induced Nonisothermal Crystallization of Ethylene-Vinyl Acetate Copolymer, Materials Letter, 58, pp. 3967-3970, 2004.

Wei et al., Structural and Properties of Nano-Hydroxyapatite/Polymer Composite Scaffolds for Bone Tissue Engineering, Biomaterials, 25, pp. 4749-4757, 2004.

Livingston, et al., A Comparative Study of Biphasic Calcium Phosphate Ceramics for Human Mesenchymal Stem-Cell-Induced Bone Formation, Biomaterials, 26, pp. 3631-3638, 2005.

Fujihara, et al., Guided Bone Regeneration Membrane Made of Polycaprolactone/Calcium Carbonate Composite Nano-fibers, Biomaterials, 26, pp. 4139-4147, 2005.

Wutticharoenmongkol, et al., Electrospinning of Polystyrene/Poly(2-methoxy-5-(2'-ethylhexyloxy)-1,4-phenylene Vinylene) Blends, Journal of Polymer Science: Part B: Polymer Physics, vol. 43, pp. 1881-1891, 2005.

Wutticharoenmongkol, Preparation and Characterization of Novel Bone Scaffolds Based on Electrospun Polycaprolactone Fibers Filled with Nanoparticles, Macromolecular Bioscience, vol. 6, pp. 70-77, 2005.

Montjovent et al., Biocompatibility of Bioresorbable Poly(L-lactic acid) Composite Scaffolds Obtained by Supercritical Gas Foaming With Human Fetal Bone Cells, Tissue Engineering 11, pp. 1640-1649, 2005.

Rezwan et al., Biodegradable and Bioactive Porous Polymer/inorganic Composite Scaffolds for Bone Tissue Engineering, Biomaterials, 27, pp. 3413-3431, 2006.

Li et al., Electrospun Silk-BMP-2 Scaffolds for Bone Tissue Engineering, Biomaterials, 27, pp. 3115-3124, 2006.

Georgiou et al., Polyactic Acid-Phosphate Glass Composite Foams as Scaffolds for Bone Tissue Engineering, J. Biomed. Mat. Res. Part B: Applied Biomaterials, Published Online Jul. 12, 2006.

Wutticharoenmongkol et al., Preparation and Characterization of Novel Bone Scaffolds Based on Electrospun Polycaprolactone Fibers Filled with Nanoparticles, Macromol. Biosci. 6, pp. 70-77, 2006.

Wutticharoenmongkol, et al., Novel Bone Scaffolds of Electrospun Polycaprolactone Fibers Filled With Nanoparticles, Journal of Nanoscience Nanotechnology, 6(2), pp. 514-522, 2006.

Thomas et al., Electrospun Bioactive Nanocomposite Scaffolds of Polycaprolactone and Nanohydroxyapatite for Bone Tissue Engineering, Journal of Nanoscience Nanotechnology, 6(2), pp. 487-493, 2006.

Venugopal et al., Biocomposite Nanofibres and Osteoblasts for Bone Tissue Engineering, Nanotechnology, 18, pp. 1-8, 2007.

Huang, Isothermal Crystallization of High-Density Polyethylene and Nanoscale Calcium Carbonate Composites, Journal of Applied Science, 107, pp. 3163-3172, 2007.

Miyazaki, et al., Crystallization Rate of Amorphous Nifedipine Analogues Unrelated to the Glass Transition Temperature, Interational Journal of Pharmaeceutics, 336, pp. 191-195, 2007.

Sun, et al. Crystallization and Thermal Properties of Polyamide 6 Composites Filled With Different Nanofillers, Materials Letters, 61, pp. 3963-3966, 2007.

Zhou et al., In Vitro Bone Engineering Based on Polycaprolactone and Polycaprolactone-Tricalcium Phosphate Composites, Polym. Int. 56, pp. 333-342, 2007.

WO 2008/157594 A3 with PCT International Search Report dated Dec. 24, 2008.

PCT International Preliminary Report on Patentability from PCT/US2008/067322 filed Jun. 18, 2008 (WO2008/157594) dated Dec. 22, 2009.

U.S. Appl. No. 14/381,493, filed Aug. 27, 2014.

Chamberlain, G. et al., Concise review: mesenchymal stem cells: their phenotype, differentiation capacity, immunological features, and potential for homing, Stem Cells, 25(11):2739-49, 2007.

Collins, M. N. et al., Comparison of the effectiveness of four different crosslinking agents with hyaluronic acid hydrogel films for tissue-culture applications, Journal of Applied Polymer Science, 104(5):3183-91, 2007.

Greco, S. et al., An interdisciplinary approach and characterization of neuronal cells transdifferentiated from human mesenchymal stem cells, Stem cells and development, 16(5):811-26, 2007.

Greco, S. J. et al., Functional similarities among genes regulated by oct-4 in human mesenchymal and embryonic stem cells, Stem Cells, 25(12):3143-54, 2007.

Greiner, et al, Electrospinning: A Fascinating Method for the Preparation of Ultrathin Fibers, Angewandte Chemie Int. Ed. Engl. 46: 5670-5703 (2007).

Karlsson, C. et al., Differentiation of human mesenchymal stem cells and articular chondrocytes: analysis of chondrogenic potential and expression pattern of differentiation-related transcription factors, Journal of Orthopaedic Research, 25:152-63, 2007.

Lack, S. et al., High-resolution nuclear magnetic resonance spectroscopy studies of polysaccharides crosslinked by sodium trimetaphosphate: a proposal for the reaction mechanism, Carbohydrate Research, 342(7):943-53, 2007.

Osiris Therapeutics Announces Positive One Year Data from Chondrogen Trial for Knee Repair, Osiris Therapeutics, Inc., Ref. Type: Internet Communication, 2007.

(56) References Cited

OTHER PUBLICATIONS http://stemcells.nih.gov/info/scireport/appendixE.asa, (visited Dec. 28, 2007; last visited Aug. 25, 2011), 6 pages.
Temple, M. M. et al., Age- and site-associate biomechanical weakening of human articular cartilage of the femoral condyle, Osteoarthritis and Cartilage, 15:1042-52, 2007.
Wi, et al., Characterization of Poly(Vinylidene Fluoride-Trifluoroethylene) 50/50 Copolymer Films as a Gate Dielectric, J. Mater Sci: Mater Electron, pp. 1-6, 2007.
Xin, X. et al., Continuing differentiation of human mesenchymal stem cells and induced chondrogenic and osteogenic lineages in electrospun PLGA nanofiber scaffold, Biomaterials, 28(2):316-25, 2007.
Bian, L. et al., Influence of chondoitin sulfate on the biochemical, mechanical and frictional properties of cartilage explants in long-term culture, Journal of Biomechanics, In press 2008.
Chen, Y. et al., Development of a chitosan-based nanoparticle formulation for delivery of a hydrophilic hexapeptide, dalargin, Biopolymers, 90(5):663-70, 2008.
Chondrogen clinical trial information for the treatment of knee injuries, Osiris Therapeutics, Inc., Ref. Type: Internet Communication, 2008.
Duffell., et al., Long-Term Intensive Electrically Stimulated Cycling by Spinal Cord-Injured People: Effect on Muscle Properties and Their Relation to Power Output, Muscle and Nerve, 38:1304-11, 2008.
Forsten-Williams, K., et al., Control of growth factor networks by heparin sulfate proteoglycans, Annals of Biomedical Engineering, 36(12):2134-48, 2008.
Kim, et al., The Role of Aligned Polymer Fiber-Based Constructs in the Bridging of Long Peripheral Nerve Gaps, Biomaterials, 29(21):3117-27, 2008.
Lankford, et al., Olfactory Ensheathing Cells Exhibit Unique Migratory, Phagocytic and Myelinating Properties in the X-Irradiated Spinal Cord Not Shared by Schwann Cells, Glia, 2008; epub ahead of print.
Liu, Z. et al., Polysaccharides-based nanoparticles as drug delivery systems, Advanced Drug Delivery Reviews, 60(15):1650-62, 2008.
Magnussen, R. A. et al., Treatment of focal articular cartilage defects in the knee: a systematic review, Clinical Orthopaedics and Related Research, 466(4):952-62, 2008.
Mueller, M. B. et al., Functional characterization of hypertrophy in chondrogenesis of human mesenchymal stem cells, Arthritis and Rheumatism, 58(5):1377-88, 2008.
PCT International Search Report and Written Opinion for PCT/US2005/043876 dated Jun. 25, 2008.
PCT International Search Report and Written Opinion for PCT/US2008/067322 dated Sep. 29, 2008.
European Search Report dated Dec. 9, 2009 for PCT/US2005/043876.
Shanmugasundaram, S. et al., Regulation of human mesenchymal stem cell chondrogenesis by scaffold geometry and mechanical properties, Society for Biomaterials Annual Meeting, 2009.
Shanmugasundaram, et al., Microscale Versus Nanoscale Scaffold Architecture for Mesenchymal Stem Cell Chondrogenesis, Tissue Engineering: Part A, vol. 60, No. 00, 2010, pp. 1-10.
PCT International Search Report and Written Opinion for PCT/US2012/050156 dated Feb. 1, 2013.
European Patent Office Action for European Patent Application No. 05852938.9 dated Jul. 1, 2014.
Hardingham, Proteoglycans: Their Structure, Interactions and Molecular Organization in Cartilage, Biochemical Society Transactions, vol. 9, No. 6, pp. 489-497, 1981.
Davis, et al., Structural and Dielectric Investigation on the Nature of the Transition in a Copolymer of Vinylidene Fluoride and Trifluoroethylene, Macromolecules, 15: 329-333, 1982.
Lovinger, Ferroelectric Polymers, Science, New Series, vol. 220, No. 4602, pp. 1115-1121, 1983.
Patel, et al., Perturbation of the Direction of Neurite Growth by Pulsed and Focal Electric Fields, Journal of Neurosci, vol. 4, pp. 2939-47, 1984.
Humphrey, et al., The Dielectric Piezoelectric and Pyroelectric Properties of VDF-TrFE Copolymers, Plessey Research (Caswell) Limited, Allen Clark Research Centre, Caswell, Towcester, Northants, NN12 8EQ, England, 1986.
Friedenstein, A. et al., Bone Marrow Osteogenetic Stem Cells: *In Vitro* Cultivation and Transplantation in Diffusion Chambers, Cell Tissue Kinet, 1987, 20(3):263-72.
Borgens, Electric Fields in Vertebrate Repair, Natural and Applied Voltage in Vertebrate Regeneration and Hearling, Wiley-Liss, 1989.
Sambrook et al., Molecular Cloning: A Laboratory Manual, $2^{nd}$ 3d., Cold Spring Harbor Laboratory, Cold Spring Harbor Laboratory Press, Cold Spring Harbor, NY, 1989. (cover page and Table of Contents for vols. 1-3).
Koga, et al., Crystallization, Field-Induced Phase Transformation, Thermally Induced Phase Transition, and Piezoelectric Activity in P(Vinylidene Fluoride-TrFE) Copolymers with High Molar Content of Vinylidene Fluoride, J. Appl. Phys, 67(2), pp. 965-974, 1990.
Safronova, et al., Characteristics of the Macromolecular Components of the Extracellular Matrix in Human Hyaline Cartilage at Different Stages of Ontogenesis, Biomedical Science, 2:162-168, 1991.
Haynesworth, S. et al., Cell Surface Antigens on Human Marrow-Derived Mesenchymal Stem Cells are Detected by Monoclonal Antibodies, J. Cell Physiol., 1992, 138:8-16.
Valentini, Electrically Charged Polymeric Substrates Enhance Nerve-Fiber Outgrowth in Vitro, Biomaterials, vol. 13, pp. 183-90, 1992.
Ausubel, et al., Current Protocols in Molecular Biology, John Wiley & Sons, New York, NY, 1993. (cover page and Table of Contentst).
Rickard, D. J. et al., Induction of Rapid Osteoblast Differentiation in Rat Bone Marrow Stromal cell Cultures by Dexamethason and BMP-2, Dev. Bio., 1994, 161:218-28.
Ohigashi, et al., Formation of "Single Crystalline Films" of Ferroelectric Copolymers of Vinylidene Fluoride and Trifluoroethylene, Appl. Phys. Lett., 66(24), pp. 3281-3283, 1995.
Kapur, et al, Human Monocyte Morphology is Affected by Local Substrate Charge Heterogeneity, J, Biomed Mater. Res., 32: 133, 1996 (abstract only).
Kapur., et al., Fabrication and Selective Surface Modification of 3-Dimensionally Textured Biomedical Polymers from Etched Silicon Substrates, Journal of Biomedical Materials Research, vol. 33, pp. 205-216 (1996).
Bouaziz, et al., Vascular Endothelial Cell Responses to Different Electrically Charged Poly(Vinylidene Fluoride) Supports Under Static and Oscillating Flow Conditions, Biomaterials, vol. 18, No. 2, 107-112, 1997.
Christie, et al., Ferroelectric and Piezoelectric Properties of a Quenched Poly(Vinylidene Fluoride-Trifluoroethylene) Copolymer, Journal of Polymer Science: Part B: Polymer Physics, vol. 35, 2671-2679, 1997.
Furukawa, Structure and Functional Properties of Ferroelectric Polymers, Advances in Colloid and Interface Science, 71-72; 183-208, 1997.
Jaiswal, N. et al., Osteogenic Differentiation of Purified Culture-Expanded Human Mesenchymal Stem Cells in vitro, J. Cell Biochem., 1997, 64:295-312.
Kadiyala, S. et al., Culture-expanded, bone marrow-derived mesenchymal stem cells can regenerate a critical-sized segmental bone defect, Tissue Engineering, 1997, 3(2):173-185.
Miraglia, S. "A Novel Five-Transmembrane Hematopoietic Stem Cell Antigen: Isolation, Characterization, and Molecular Cloning," *Blood* 90:5013-21 (1997).
Omote, et al., Temperature Dependence of Elastic, Dielectric, and Piezoelectric Properties of "Single Crystalline" Films of Vinylidene Fluoride Trifluoroethylene Copolymer, J. Appl. Phys., 81(6), pp. 2760-2769, 1997.
Schmidt, et al., Stimulation of Neurite Outgrowth Using an Electrically Conducting Polymer, Proc. Natl. Acad. Sci, vol. 94, pp. 8948-8953, 1997.

(56) References Cited

OTHER PUBLICATIONS

Virts, E. et al. "Murine Mast Cells and Monocytes Express Distinctive Sets of CD45 Isoforms," Immunology 34(16-17):1119-97 (1997).

Yin, A.H. "AC133, A Novel Marker for Human Hematopoietic Stem and Progenitor Cells," Blood 90:500212 (1997).

Bruder, S. P. et al., Bone Regeneration by Implantation of Purified, Culture-Expanded Human Mesenchymal Stem Cells, J. Orthop. Res., 1998, 16:155-162.

Bune, et al., Two-Dimensional Ferroelectric Films, Nature, vol. 391, 874-877, 1998.

Mackay, a. M. et al., Chrondrogenic Differentiation of Cultured Human Mesenchymal Stem Cells From Marrow, Tissue Engineering, 1998, 4(4):415-428.

Zhao, et al., Electromechanical Properties of Electrostrictive Poly(Vinylidene Fluoride-Trifluoroethylene) Copolymer, Applied Physics Letters, vol. 73, No. 14, pp. 2054-2056, 1998.

Borgens, Electrically Mediated Regeneration and Guidance of Adult Mammalian Spinal Axons into Polymeric Channels, Neuroscience, 91(1):251-64; 1999.

Laurencin, C.T. "Tissue Engineering: Orthopedic Applications," Ann. Rev. Biomed. Eng'g 1:19-46 (1999).

Pittenger, M. F. et al., Multilineage Potential of Adult Human Mesenchymal Stem Cells, Science, 1999, 284:143-7.

Praemer, A., Musculoskeletal Conditions in the United States, American Academy of Orthopaedic Surgeons, 1999, p. 34-39.

Stinger et al., Joint cartilage regeneration by tissue engineering, Z. Rheumatol 1999; 58:130-5.

Browne, J. E. et al., Surgical alternatives for treatment of articular cartilage lesions, J. Am. Acad. Orthop. Surg., 2000, 8(3):180-9.

DeLise, A. M. et al., Cellular Interactions and Signaling in Cartilage Development, Osteoarthritis and Cartilage, 2000, 8:309-34.

Fuchs, et al., Stem Cells: A New Lease on Life, Cell 100: 143-155 (2000).

Hilczer, et al., The Method of Matching Resonance Frequencies in Coupled Transmitter PVDF/TRFE Diaphragms, IEEE Transactions on Dielectrics and Electrical Insulation, vol. 7, No. 4, pp. 498-502, 2000.

Ponticello et al., Gelatin-Based Resorbable Sponge As a Carrier Matrix for Human Mesenchymal Stem Cells in Cartilage Regeneration Therapy, J Biomed Materials Res 52: 246-255 (2000).

Watt , et al., Out of Eden: Stem Cells and Their Niches, Science 287:1427-1430 (2000).

Xie, et al., A Niche Maintaining Germ Line Stem Cells in Drosophila Ovary, Science 290:328-330, 2000.

Barry, et al., Chondrogenic Differentiation of Mesenchymal Stem Cells from Bone Marrow: Differentiation-Dependent Gene Expression of Matrix Components, Experimental Cell Research, 268:189-200 (2001).

Brook et al., Columns of Schwann Cells Extruded Into the CNS Induce In-Growth of Astrocytes to Form Organized New Glial Pathways, GLIA, 33:118-130, 2001.

Christensen, N. D. et al., Papillomavirus Microbicidal Cctivities of High-Molecular-Weight Cellulose Sulfate, Dextran Sulfate, and Polystyrene Sulfonate, Antimicrobial Agents and Chemotherapy, 2001, 45(12):3427-32.

Guo et al., Biological features of mesenchymal stem cells from human bone marrow, Chinese Med J. 2001, 114:950-3.

Harrison, et al., Piezolelectric Polymers, ICASE, NASA Langley Research Center, Hampton, Virginia, NASA/CR-2001-211422, ICASE Report No. 2001-43, pp. 1-26, 2001.

Ishihara, M. et al., Heparin-Carrying Polystyrene (HCPS)-Bound Collagen Substratum to Immobilize Heparin-Binding Growth Factors and to Enhance Cellular Growth, J. Biomed. Mat. Res., 2001, 56(4):536-44.

Koombhongse, et al., Flat Polymer Ribbons and Other Shapes by Electrospinning, Journal of Polymer Science: Part B: Polymer Physics, vol. 39, 2598-2606, 2001.

Kotwal, et al., Electrical Stimulation Alters Protein Adsorption and Nerve Cell Interactions With Electrically Conducting Biomaterials, Biomaterials, 22: 1055-1064, 2001.

N.S.C.I.A., Spinal Cord Injury Fact Sheet, Birmingham, 2001; http://users.erols.com/nscia/resource/factshts/.

Negishi, Optic Nerve Regeneration Within Artificial Schwann Cell Graft in the Adult Rat, Brain Research Bulletin, 55:409-419, 2001.

Ploss, et al., Poling Study of PZT/P(VDF-TrFE) Composites, Composites Science and Technology, 61, 957-962, 2001.

Rahman et al., Enhancement of Chondrogenic Differentiation of Human Articular Chondrocytes by Biodegradable Polymers, Tissue Engineering; 2001; 7:781-90.

Rogovina, S. Z. et al., Solid State Production of Cellulose-Chitosan Blends and their Modification and the Diglycidyl Ether of Oligo(ethylene oxide), Polymer Degradation and Stability, 2001, 73(3):557-60.

Yannas IV, Tissue and Organ Regeneration in Adults, Springer, 2001(cover page and Table of Contents).

Anderson, R. A. et al., Preclinical Evaluation of Sodium Cellulose Sulfate (Ushercell) as a Contraceptive Antimicrobial Agent, Journal of Andrology, 2002, 23(3):426-38.

Arinzeh, T. et al., In vivo Evaluation of a Bioactive Scaffold for Bone Tissue Engineering, J. Biomed. Mat. Res., 2002, 62:1-13.

Dozin, B. et al., Response of young, aged and osteoarthritic human articular chondrocytes to inflammatory cytokines: molecular and cellular aspects, Matrix Biology, 2002, 21(5):449-59.

Muller, P. Y. et al., Processing of gene expression data generated by quantitative real-time RT-PCR, Biotechniques, 2002, 32(6):1372-4.

Nettles et al., Potential Use of Chitosan as a Cell Scaffold Material for Carilage Tissue Engineering, Tissue Engineering, Vo. 8, No. 6, pp. 1009-1016, 2002.

Arinzeh, T. et al, Allogeneic mesenchymal stem cells regenerate bone in a critical-sized canine segmental defect, Journal of Bone and Joint Surgery American, 2003, 85-A(1):1927-35.

Benz, et al., Determination of the Crystalline Phases of Poly(Vinylidene Fluoride) Under Different Preparation Conditions Using Differential Scanning Calorimetry and Infrared Spectroscopy, Journal of Applied Polymer Science, vol. 89, 1093-1100, 2003.

Endres et al., Osteogenic Induction of Human Bone Marrow-Derived Mesenchymal Progenitor Cells in Novel Synthetic Polymer-Hydrogel Matrices, Tissue Engineering, vol. 9, No. 4, pp. 689-702, 2003.

Livingston, et al., Mesenchymal Stem Cells Combined With Biphasic Calcium Phosphate Ceramics Promote Bone Regeneration, Journal of Materials Science: Materials in Medicine, 14: 211-218 (2003).

Luu et al., "Development of a Nanostructured DNA Delivery Scaffold via Electrospinning of PLGA and PLA-PEG block copolymers". Journal of Controlled Release, 2003, vol. 89, pp. 341-353.

Murphy et al., Stem Cell Therapy in a Caprine Model of Osteoarthritis, Arthritis Rheumatism 48: No. 12, 3464-3474 (2003).

Sachlos, et al., Making Tissue Engineering Scaffolds Work, Review of the Application of Solid Freeform Fabrication Technology to the Production of Tissue Engineering Scaffolds, European Cells & Materials 5: 29-40 (2003).

Seoul, et al., Electrospinning of Poly(Vinylidene Fluoride)/Dimethylformamide Solutions With Carbon Nanotubes, Journal of Polymer Science: part B: Polymer Physics, vol. 41, 1572-1577, 2003.

Sikavitsas et al., "Mineralized Matrix Deposition by Marrow Stromal Osteoblasts in 3D Perfusion Culture Increases With Increasing Fluid Shear Forces". PBAS, Dec. 9, 2003, vol. 100, No. 25, pp. 14683-14688.

Wan-Ju, et al., Biological Response of Chondrocytes Cultrued in Three-Dimensional Nanofibrous Poly(caprolactone) Scaffolds, J. Biomed. Mater. Res. 67A:1105-1114, 2003.

Yeh, E.T.H. et al., "Transdifferentiation of Human Peripheral Blood CD34+-Enriched Cell Population Into Cardiomyocytes, Endothelial Cells, and Smooth Muscle Cells in Vivo," Circulation 108:2070-73, 2003.

Zong et al., Electrospun Non-woven Membranes As Scaffolds for Heart Tissue Constructs. 226th ACS National Meeting, 2003. 2003.

(56) References Cited

OTHER PUBLICATIONS

Bhattarai, et al., Novel Biodegradable Electrospun Membrane: Scaffold for Tissue Engineering, Biomaterials, vol. 25, No. 13, pp. 2595-2602, 2004.
Bryan, et al., Enhanced Peripheral Nerve Regeneration Through a Poled Bioresorbable Poly(Lactic-co-glycolic Acid) Guidance Channel, J. Neural Eng., 1, 91-98, 2004.
Chen, et al., Chondrogenic differentiation of Human Mesenchymal Stem Cells Cultured in a Cobweb-Like Biodegradable Scaffold, Biochemical and Biophysical Research Communications, 322, pp. 50-55 (2004).
Dezawa, Specific Induction of Neuronal Cells From Bone Marrow Stromal ells and Application for Autologous Transplantation, Journal of Clinical Investigation; 113:1701-1710, 2004.
Jin et al., "Human Bone Marrow Stromal Cell Responses On Electrospun Silk Fibroin Mats", Biomaterials, 2004, vol. 25, pp. 1039-1047.
Rosenzweig, et al., Rodent Models for Treatment of Spinal Cord Injury: Research Trends and Progress Toward Useful Repair, Current Opinion in Neurology, 17(2); 121-31, 2004.
Shanmugasundaram, et al., Applications of Electrospinning: Tissue Engineering Scaffolds and Drug Delivery System, Bioengineering, Proceedings of the Northeast Conference, vol. 30, pp. 140-141, 2004.
Shields, K. J. et al., Mechanical properties and cellular proliferation of electrospun collagen Type II, Tissue Engineering, 2004, 10(9-10):1510-7.
Stinger et all., Current Strategies for Cell Delivery in Cartilage and Bone Regeneration, Current Opinion in Biotechnology, vol. 115, Issue 5, pp. 411-418, 2004.
You, J. O. et al., Calcium-alginate nanoparticles formed by reverse microemulsion as gene carriers, macromolecular Symposia, 2004, 219(147):153.
Aroen, A. et al, "Articular Cartilage Defects in a Rabbit Model, Retention Rate of Periosteal Flap Cover", Acta Orthrop. 76(2):220-4, 2005.
Browne, J. E. et al., Clinical outcome of autologous chondrocyte implantation at 5 years in US subjects, Clinical Orthopaedics and Related Research, 2005, 436:237-45.
Clar, C. et al., Clinical and cost-effectiveness of autologous chondocyte implantation for cartilage defects in knee joints: systematic review and economic evaluation, Health Technology Assessment, 2005, 9(47):four pages.
Cummings, et al., Human Neural Stem Cells Differentiate and Promote Locomoter Recovery in Spinal Cord-Injured Mice, Proceedings of the National Academy of Sciences, 102(39):14069-74, 2005.
Ducharme, et al., Ferroelectric Polymeric Langmuir-Blodgett Films for Non-Volatile Memory Applications, Nebraska Research Initiative, the National Science Foundation and the Office of Naval Research, Department of Physics and Astronomy and the Center for Materials Research and Analysis at the University of Nebraska, Lincoln, NE, pp. 1-41, 2005.
Holmes, N. "CD45: All is Not Yet Crystal Clear", Immunology 117:145-155, 2005.
Kang, S. W. et al., Ply(lactic-co-glycolic acid) microspheres as an injectible scaffold for cartilage tissue engineering, Tissue Engineering, 2005, 11(3-4):438-47.
Klein, et al., Influence of Composition on Relaxor Ferroelectric and Electromechanical Properties of Poly(Vinyliden Fluoride-Trifluoroethylene-Chlorofluoroethylene), Journal of Applied Physics, 97, 094105, pp. 1-4, 2005.
Laxminarayana, et al., Functional Nanotube-Based Textiles: Pathyway to Next Generation Fabrics With Enhanced Sensing Capabilities, Textile Res. J., 75(9), 670-680, 2005.
Li, Wan-Ju et al., Multilineage Differentiation of Human Mesenchymal Stem Cells in a Three-Dimensional Nanofibrous Scaffold, Biomaterials, vol. 26, No. 25, pp. 5158-5166, 2005.
Maire, M. et al., Retention of transforming growth factor using functionalized dextran-based hydrogels, Biomaterials, 26(14):1771-80, 2005.
Naber, et al., Low-Voltage Programmable Ferroelectric Polymer Field-Effect Transistors, Applied Physics Letters, 87: 203509, pp. 51-57, 2005.
Schaffellner, S. et al., Porcine islet cells microencapsulated in sodium cellulose sulfate, Transplantation Proceedings, 2005, 37(1):248-52.
Shapiro, et al., Oscillating Field Stimulation for Complete Spinal Cord Injury in Humans: A Phase 1 Trial, Journal of Neurosurgery Spine, 2005:2(1):3-10.
Zhang et al., Tissue-Engineering Approaches for Axonal Guidance, Brain Res. Brain Res. Rev, vol. 49, pp. 4864, 2005.
Zhao, et al., Preparation and Properties of Electrospun Poly(Vinylidene Fluoride) Membranes, Journal of Applied Polymer Science, vol. 97, 466-474, 2005.
Beloti, et al., In Vitro Biocompatibility of a Novel Membrane of the Composite Poly(Vinylidene-Trifluoroethylene)/Barium Titanate, InterScience Journal of Biomedical Materials Research Part A, 281-288, 2006.
Cizkova, et al., Transplants of Human Mesenchymal Stem Cells Improve Functional Recovery After Spinal Cord Injury in the Rat, Cellular and Molecular Neurobiology, 26(7/8):1167-80, 2006.
Gama, C. L., Sulfation patterns of glycosaminoglycans encode molecular recognition and activity, Nature Chemical Biology, 2006, 2(9):467-73.
Himes, et al., Recovery of Function Following Grafting of Human Bone Marrow-Derived Stromal Cells Into the Injured Spinal Cord, Neurorehabilitation and Neural Repair, 20:278-96, 2006.
Hung, et al., The Effect of Chitosan and PVDF Substrates on the Behavior of Embryonic Rat Cerebral Cortical Stem Cells, Biomaterials, 27, 4461-4469, 2006.
Kuo, C. K. et al., Cartilage tissue engineering: its potential and uses, Current Opinion in Rheumatology, 2006, 18(1):64-73.
Nasir, et al., Control of Diameter, Morphology, and Structure of PVDF Nanofiber Fabricated by Electrospray Deposition, Journal of Polymer Science: Part B: Polymer Physics, vol. 44, 779-786, 2006.
Oudega, et al., Schwann Cell Transplantation for Repair of the Adult Spinal Cord, Journal of Neurotrauma, 23(3-4), 453-67, 2006.
Pelttari, K. et al., Premature induction of hypertrophy during in vitro chondrogenesis of human mesenchymal stem cells correlates with calcification and vascular invasion after ectopic transplantation in SCID mice, Arthritis and Rheumatism, 54:3254-66, 2006.
Shanmugasundaram, S. et al., The Effect of Varying the Architecture of Scaffolds on Mesenchymal Stem Cell Osteogenesis and Chondrogenesis, Transactions of the 2006 Annual Meeting of the Society for Biomaterials, 2006.
Stiegler, P. B. et al., Cryopreservation of insulin-producing cells microencapsulated in sodium cellulose sulfate, Transplantation Proceedings, 38(9):3026-30, 2006.
Tashiro, et al, Structural Correlation Between Crystal Lattice and Lamellar Morphology in the Ferroelectric Phase Transition of Vinylidene Fluoride-Trifluoroethylene Copolymers as Revealed by the Simultaneous Measurements of Wide-Angle and Small-Angle X-Ray Scatterings, Polymer, 47, 5433-5444, 2006.
Wu, et al., Poly(Vinylidene Fluoride)/Polyethersulfone Blend Membranes: Effects of Solvent Sort, Polyethersulfone and Polyvinylpyrrolidone Concentration on Their Properties and Morphology, Journal of Membrane Science, 285, 290-298, 2006.
Yang, et al., Preparation of Bioelectret Collagen and Its Influence on Cell Culture In Vitro, J. Mater. Sci: Mater Med, 17:767-771, 2006.
Catalani, et al., Evidence for Molecular Orientation and Residual Charge in the Electrospinning of Poly (Butylenes Terephthalate) Nanofibers, Macromolecules, vol. 40, pp. 1693-7, 2007.

* cited by examiner

ELECTROSPUN CERAMIC-POLYMER COMPOSITE AS A SCAFFOLD FOR TISSUE REPAIR

CROSS-REFERENCE TO RELATED APPLICATIONS

This Application is a divisional of U.S. application Ser. No. 12/141,340 filed on Jun. 18, 2008, which application claims the benefit of U.S. Provisional Application No. 60/944,587 entitled "Electrospun Ceramic-Polymer Composite as a Scaffold for Tissue Repair," filed Jun. 18, 2007, the entirety of which is incorporated herein by reference.

GOVERNMENT SUPPORT

This work is supported at least in part by grants to Dr. Arinzeh. The government may have certain rights in this invention.

FIELD OF THE INVENTION

The present invention relates to compositions and methods of preparing a three-dimensional matrix of micron sized electrospun fibers, wherein the electrospun fibers are formed from an electrospun composite comprising a bioactive ceramic component and a polymer component. The matrix provides an osteoconductive and osteoinductive scaffold supporting osteogenesis and thereby facilitates bone repair.

BACKGROUND OF THE INVENTION

The repair of large bone defects resulting from trauma, metabolic disorders, and tumor removal is a major medical challenge. Typically, such defects are treated with a bone allograft, where the terms "allograft" or "allogeneic transplant" are used interchangeably to refer to situations in which transplanted cells, tissues, or organs are sourced from a genetically non-identical member of the same species. However, allografts lack osteoinductive factors necessary to accelerate new bone growth and may carry the risk of disease transmission, since such grafts typically are harvested from cadavers. Due to these limitations, alternative strategies are needed.

Tissue engineering is one approach to the repair of large bone defects that has gained considerable interest. Tissue engineering is the application of principles and methods of engineering and life sciences toward a fundamental understanding and development of biological substitutes to restore, maintain and improve human tissue functions. Bone regeneration may be achieved by the use of osteogenic cells and/or factors to induce bone growth in combination with an appropriate scaffold to guide and support the laying down of new bone tissue. Optimally, a scaffold for bone tissue engineering should satisfy the following minimum requirements: biocompatibility (meaning the ability to coexist with living tissues or organisms without causing harm), osteoconductivity (meaning the ability to serve as a scaffold or matrix on which bone cells may attach, migrate and form new bone), porosity (meaning having minute openings, pores or holes that may be filled (permeated) by water, air or other materials), biodegradability (meaning having the ability to break down into harmless substances by the action of living organisms) and mechanical integrity (meaning having the ability to hold together and withstand chemical, physical, and biological forces over time).

The term "bioceramic" refers to ceramic materials employed within the body. Bioceramics employed within the body may be inert (meaning they remain unchanged), resorbable (meaning they dissolve) or active (meaning they may take part actively in physiological processes). Bioceramics may take many forms, including, but not limited to, microspheres, thin layers or coatings, porous networks, composites having a polymer component, and large well-polished surfaces. Direct use of ceramics for clinical applications has been limited because of their brittleness and difficulty in shaping.

Generally, those of skill in the art combine one ceramic and one polymer to create scaffolds appropriate for bone tissue engineering. K. Rezwan et al., *Biodegradable and bioactive porous polymer/inorganic composite scaffolds for bone tissue engineering*, Biomaterials 27 (2006) 3413-3431.

Several methods have been used to synthesize tissue engineering scaffolds based on polycaprolactone and polycaprolactone-tricalcium phosphate composites. For example, Zhou et al (*In vitro bone engineering based on polycaprolactone and polycaprolactone-tricalcium phosphate composites*, Polym Int 56 (2007) 333-342) used a fused deposition modeling method to synthesize a composite of poly(ε-caprolactone) (PCL) and tricalcium phosphate (TCP). Although a foaming method has been used to create hydroxyapatite-poly(L-lactic acid) ((HA)-(PLLA)) and β-TCP-poly(lactic acid) (β-TCP-PLA) composites M. Montjovent et al. *Biocompatibility of bioresorbable poly(L-lactic acid) composite scaffolds obtained by supercritical gas foaming with human fetal bone cells*, Tissue Engineering 11 (2005) 1640-1649, the authors did not create a composite of PLA, HA, and β-TCP together. G. Georgiou et al., *Polylactic acid phosphate glass composite foams as scaffolds for bone tissue engineering*, J. Biomed. Mat. Res. Part B: Applied Biomaterials, published online Jul. 12, 2006, used a foaming or compression molding method to synthesize a composite of PLA and a phosphate. See also, U.S. Pat. No. 5,626,861; U.S. Pat. No. 5,681,873, U.S. Pat. No. 5,766,618 (the '618 patent), U.S. Pat. No. 5,955, 529; U.S. Pat. No. 6,165,486; U.S. Pat. No. 6,306,424; U.S. Pat. No. 6,730,252; U.S. Pat. No. 7,012,106; U.S. Pat. No. 7,022,522. None of these contemplate the use of electrospinning as a method to synthesize a scaffold containing ceramic polymer composites.

Electrospinning, another method that has been used to synthesize polymeric tissue engineering scaffolds, applies a high voltage to an ejectable polymer solution. The basic principle behind this process is that an electric voltage sufficient enough to overcome the surface tension of a polymeric solution causes the polymer droplets to elongate so that the polymer is splayed randomly as very fine fibers, which when collected on a grounded metal plate, form non-woven mats. Traditionally, electrospinning has yielded nonwoven mats (also called matrices and scaffolds) of nanometer sized fiber diameters and nanometer sized pore diameters. However, in order for cells to infiltrate into a scaffold and proliferate, micron sized fiber diameters and micron sized pore diameters are optimal. Since the diameter of a cell is approximately 10 μm to 20 μm, pore sizes at the cellular level or above are needed to allow for cell infiltration.

Polymer and calcium phosphate ceramic composites used in conventional scaffold-forming techniques are not easily adaptable to the electrospinning method. The parameters of voltage, flow rate, needle gauge size, distance to collection plate, and polymer solution concentration during processing need to be optimized to achieve fibrous mats. When combining a polymer with a ceramic in solution, in addition to optimizing these parameters, the homogeneity of the polymer-ceramic mixtures must be ensured. Moreover, the literature in this field does not provide sufficient guidance to enable one of skill in the art of tissue engineering to adapt polymer and ceramic composites to the electrospinning method using routine experimentation.

Previous work to develop scaffold materials for tissue engineering by electrospinning using polycaprolactone (PCL) or hydroxyapatite (HA) has produced mats containing nanometer sized fiber diameters having nanosized pore diameters in the mat. Such mats are not optimal for osteogenesis, because these pore diameters are below the preferred range of pore sizes for cell infiltration. See e.g. H. Yoshimoto et al., *A biodegradable nanofiber scaffold by electrospinning and its potential for bone tissue engineering*, Biomaterials 24 (2003) 2077-2082; M. Shin et al., *In vivo bone tissue engineering using mesenchymal stem cells on a novel electrospun nanofibrous scaffold*, Tissue Engineering 10 (2004) 33-41; C. Li et al., *Electrospun silk-BMP-2 scaffolds for bone tissue engineering*, Biomaterials 27 (2006) 3115-3124. HA also has been electrospun with PCL alone (P. Wutticharoenmongkol et al., *Preparation and characterization of novel bone scaffolds based on electrospun polycaprolactone fibers filled with nanoparticles*, Macromol. Biosci. 6 (2006) 70-77) and with PCL and collagen (J. Venugopal et al., *Biocomposite nanofibres and osteoblasts for bone tissue engineering*, Nanotechnology 18 (2007) 1-8).

Likewise, a number of patents have disclosed an electrospinning method for production of polymer nanofibers. These nanofiber mats have nanosized pore diameters in the mat, which are below the desired range of pore sizes necessary for cell infiltration. See, for example, U.S. Pat. No. 6,689,166; U.S. Pat. No. 6,790,528; U.S. Published Pat. App. No. 2004/0018226; U.S. Published Pat. App. No. 2006/0204539; U.S. Published Pat. App. No. 2006/0128012.

In order for a biodegradable scaffold to be successful, the material must have a rate of degradation that is commensurate with the growth of new bone. Ideally, the scaffold should degrade slowly enough to maintain structural support during the initial stages of bone formation, but fast enough to allow space for continuous growth of new bone. Previous studies have demonstrated the potential of biphasic compositions of HA and β-TCP ceramics for bone tissue engineering applications. One major advantage is that their rate of degradation correlates with bone tissue formation.

The present invention, which addresses this problem, provides compositions and methods of preparing a three-dimensional matrix of micron sized electrospun fibers, wherein the electrospun fibers are formed from a electrospun composite comprising a bioactive ceramic component and a polymer component. The matrix provides an osteoconductive and osteoinductive scaffold supporting osteogenesis and thereby may facilitate bone repair.

SUMMARY OF THE INVENTION

In one aspect, the present invention provides an implantable scaffold for use in tissue engineering comprising a three-dimensional matrix of micron sized electrospun fibers, wherein the electrospun fibers are formed from an electrospun composite comprising a bioactive ceramic component and a polymer component. According to one embodiment, the electrospun composite of the implantable scaffold contains at least 10% by weight of the ceramic component. According to another embodiment, the electrospun composite of the implantable scaffold contains at least about 60% by weight of the polymer component. According to another embodiment, the electrospun composite of the implantable scaffold contains at least 10% by weight of the ceramic component and at least about 60% by weight of the polymer component. According to another embodiment, the bioactive ceramic component of the electrospun composite of the implantable scaffold contains two calcium phosphate ceramic substances for every polymer in the polymer component of the composite. According to another embodiment, the calcium phosphate ceramic substances of the bioactive ceramic component of the electrospun composite are selected from the group consisting of tetracalcium phosphate, amorphous calcium phosphate, alpha-tricalcium phosphate, beta-tricalcium phosphate, and hydroxyapatite. According to another embodiment, the two calcium phosphate ceramic substances of the bioactive ceramic component of the electrospun composite are hydroxyapatite and tricalcium phosphate. According to another embodiment, the bioactive ceramic component of the electrospun composite comprises 20% hydroxyapatite and 80% tricalcium phosphate. According to another embodiment, the polymer component of the electrospun composite is at least one polymer selected from the group consisting of a nondegradable polymer and a a degradable polymer. According to another embodiment, the nondegradable polymer is selected from the group consisting of a polyurethane, a polyvinylidine fluoride, and a polyvinylidine fluoride trifluoroethylene. According to another embodiment, the degradable polymer is selected from the group consisting of poly(lactic acid-glycolic acid), poly(lactic acid), poly(glycolic acid), a poly(orthoester), a poly(phosphazene), a polycaprolactone, a polyamide, a polysaccharide, and a collagen. According to another embodiment, the polymer of the polymer component of the electrospun composite is polycaprolactone. According to another embodiment, the three dimensional matrix of electrospun fibers of the implantable scaffold comprises micron-sized pores.

In another aspect, the present invention provides a composition for preparing an implantable osteogenic three-dimensional matrix of micron sized electrospun fibers, the composition comprising an electrospun composite containing a bioactive ceramic component and a polymer component. According to one embodiment, the electrospun composite of the composition contains at least 10% by weight of the ceramic component. According to another embodiment, the electrospun composite of the composition contains at least about 60% by weight of the polymer component. According to another embodiment, the electrospun composite of the composition contains at least 10% by weight of the ceramic component and at least about 60% by weight of the polymer component. According to another embodiment, the bioactive ceramic component of the electrospun composite of the composition contains two calcium phosphate ceramic substances for every polymer in the polymer component of the composite. According to another embodiment, the calcium phosphate ceramic substances of the bioactive ceramic component of the electrospun composite of the composition are selected from the group consisting of tetracalcium phosphate, amorphous calcium phosphate, alpha-tricalcium phosphate, beta-tricalcium phosphate, and hydroxyapatite. According to another embodiment, the two calcium phosphate ceramic substances of the bioactive ceramic component of the electrospun composite of the composition are hydroxyapatite and tricalcium phosphate. According to another embodiment, the bioactive ceramic component of the electrospun composite of the composition comprises 20% hydroxyapatite and 80% tricalcium phosphate. According to another embodiment, the polymer component of the electrospun composite is at least one polymer selected from the group consisting of a nondegradable polymer and a a degradable polymer. According to another embodiment, the nondegradable polymer is selected from the group consisting of a polyurethane, a polyvinylidine fluoride, and a polyvinylidine fluoride trifluoroethylene. According to another embodiment, the degradable polymer is selected from the group consisting of poly(lactic acid-glycolic acid), poly(lactic acid), poly(glycolic acid), a poly(orthoester), a poly(phosphazene), a polycaprolactone, a polyamide, a polysaccharide, and a collagen. According to another embodiment, the polymer of the polymer component of the electrospun composite of the composition is polycaprolactone.

In another aspect, the present invention provides a method of preparing a osteoinductive scaffold to facilitate bone repair, the method comprising the steps: (a) preparing a ceramic-polymer composite comprising a bioactive ceramic component and a polymer component; (b) electrospinning the ceramic-polymer composite, and thereby (c) depositing a three-dimensional nonwoven matrix of electrospun fibers comprising the ceramic-polymer composite on a collector. According to one embodiment of the method, the electrospun composite of step (a) contains at least 10% by weight of the ceramic component. According to another embodiment of the method, the electrospun composite of step (a) contains at least about 60% by weight of the polymer component. According to another embodiment of the method, the electrospun composite contains at least 10% by weight of the ceramic component and at least about 60% by weight of the polymer component. According to another embodiment of the method, the bioactive ceramic component of the composite of step (a) contains two calcium phosphate ceramic substances for every polymer in the polymer component of the composite. According to another embodiment of the method, the calcium phosphate ceramic substances of the bioactive ceramic component of the composition of step (a) are selected from the group consisting of tetracalcium phosphate, amorphous calcium phosphate, alpha-tricalcium phosphate, beta-tricalcium phosphate, and hydroxyapatite. According to another embodiment of the method, the two calcium phosphate ceramic substances of the bioactive ceramic component of step (a) are hydroxyapatite and tricalcium phosphate. According to another embodiment of the method, the bioactive ceramic component of the composite of step (a) comprises 20% hydroxyapatite and 80% tricalcium phosphate. According to another embodiment of the method, the polymer component of the composite of step (a) is at least one polymer selected from the group consisting of a nondegradable polymer and a degradable polymer. According to another embodiment, the nondegradable polymer is selected from the group consisting of a polyurethane, a polyvinylidine fluoride, and a polyvinylidine fluoride trifluoroethylene. According to another embodiment, the degradable polymer is selected from the group consisting of poly(lactic acid-glycolic acid), polylactic acid), poly(glycolic acid), a poly(orthoester), a poly(phosphazene), a polycaprolactone, a polyamide, a polysaccharide, and a collagen. According to another embodiment of the method, the polymer of the polymer component of the composite of step (a) is polycaprolactone. According to another embodiment of the method, the electrospun fibers of step (c) are micron sized. According to another embodiment of the method, the matrix of electrospun fibers in step (c) comprises micron-sized pores. According to another embodiment of the method, the method further comprises the steps: (d) seeding the three-dimensional nonwoven matrix of electrospun fibers with isolated differentiable human mesenchymal cells or osteoblasts; and (e) growing the differentiable human mesenchymal cells or osteoblasts on the three-dimensional nonwoven matrix of electrospun fibers so that the differentiable human mesenchymal cells or osteoblasts differentiate into a mature cell phenotype on the scaffold.

DETAILED DESCRIPTION OF THE INVENTION

Figure 1:
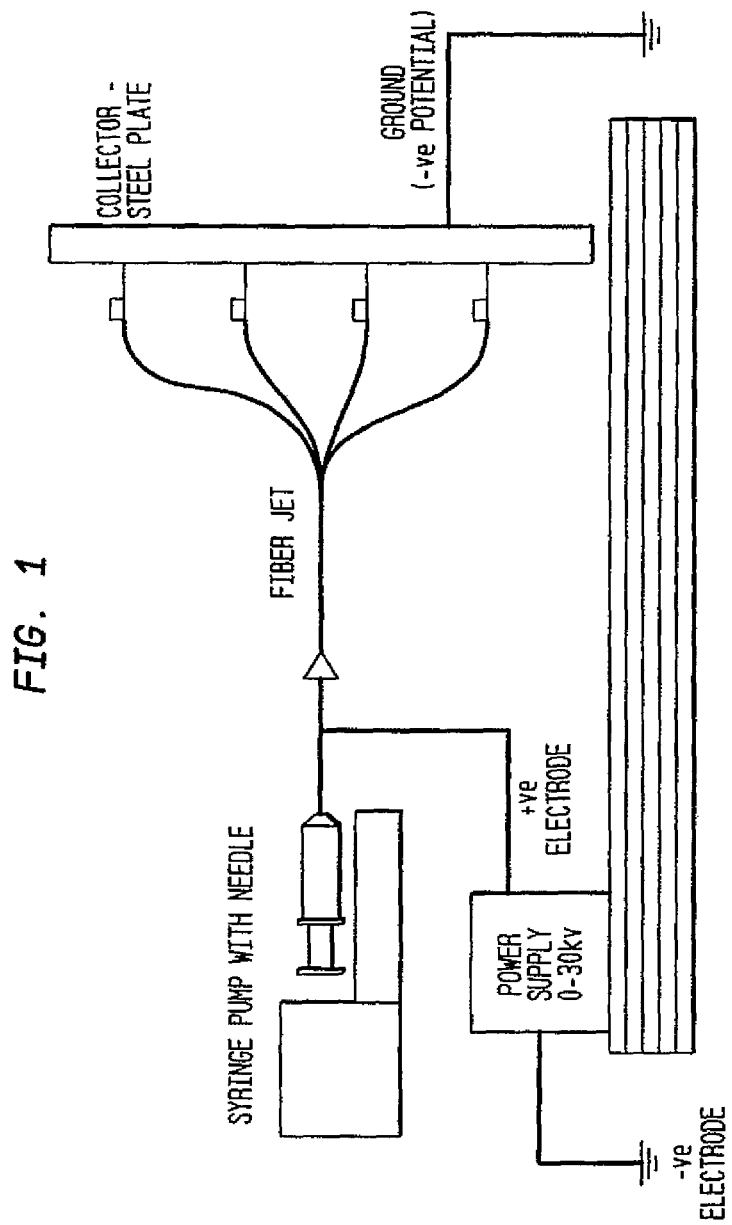
FIG. 1 is a diagrammatic representation of the electrospinning equipment used herein.

The present invention provides an electrospun scaffold of bioactive ceramic materials having micron sized fiber diameters and pores and a method of preparing such scaffolds. The pore size diameters of the micron sized fibers in the scaffold provide for improved cell infiltration, aggregation, and tissue formation throughout the scaffold when compared with nano-sized fibers.

As used herein, the term "Beta-Tricalcium Phosphate" ("β-TCP") refers to a synthetic material whose formula is $Ca_3(PO_4)_2$.

As used herein, the terms "bioactive" and "bioactivity" are used interchangeably to refer to any effect on, interaction with, or response from living tissue.

As used herein, the term "biocompatible material" refers to a material that the body generally accepts without a major immune response, which is capable of implantation in biological systems, for example, tissue implantation, without causing excessive fibrosis or rejection reactions. As used herein, the term "biodegradable" refers to the ability of a substance or material to break down into harmless substances by the action of living organisms.

The term "collagen" refers to any of a family of extracellular, closely related proteins occurring as a major component of connective tissue, giving it strength and flexibility. At least 14 types exist, each composed of tropocollagen units that share a common triple-helical shape but that vary somewhat in composition between types, with the types being localized to different tissues, stages, or functions. In some types, including the most common, Type I, the tropocollagen rods associate to form fibrils or fibers; in other types the rods are not fibrillar but are associated with fibrillar collagens, while in others they form nonfibrillar, nonperiodic but structured networks. Tropocollagen, the basic structural unit of collagen comprises a helical structure consisting of three polypeptide chains, each chain composed of about a thousand amino acids, coiled around each other to form a spiral and stabilized by inter- and intrachain covalent bonds. It is rich in glycine, which occurs as nearly one residue out of three, as well as proline, hydroxyproline, and hydroxylysine; the last two rarely occur in other proteins.

The terms "microscale fiber" or "micron sized fiber" are used interchangeably to refer to fibers whose diameter ranges from about 1 micrometer ($10^{-6}$ m) to about 1000 micrometers. The terms "nanoscale fiber" or "nano sized fiber" are used interchangeably to refer to fibers whose diameter ranges from about 1 nanometer ($10^{-9}$ m) to about 1000 nanometers.

The term "osteoconduction" or "osteoconductive" as used herein refers to a material having the ability to serve as a scaffold on which bone cells may attach, migrate and form new bone.

The term osteoinduction or "osteoinductive" as used herein refers to a material having the ability to induce bone to grow.

The term "polymer" as used herein refers to a macromolecule formed by the chemical union of five or more identical combining units called monomers. In most cases, the number of monomer is quite large and often is not precisely known. In synthetic polymers, this number may be controlled to a predetermined extent. Combinations two, three, or four monomers are called, respectively, dimers, trimers, and tetramers, and are known collectively as oligomers. Polymers may be inorganic (e.g., siloxane, sulfur chains, black phosphorus, boron-nitrogen, silicones) or organic (meaning containing carbon). Organic polymers may be natural [e.g., polysaccharides, such as starch, cellulose, pectin, seaweed gums, vegetable gums; polypeptides, such as casein, albumin, globulin, keratin, insulin, DNA; and hydrocarbons], synthetic [such as thermoplastics (unvulcanized elastomers, nylon, polyvinyl chloride, linear polyethylene, polystyrene, polypropylene, polyurethane, acrylate resins); thermosetting (e.g., vulcanized elastomers, crosslinked polyethylene, phenolics, alkyds, polyesters), and semisynthetic (e.g., cellulosics, such as rayon, methylcellulose, cellulose acetate; and modified starches)].

The term "polyamide" refers to a polymer containing monomers joined by amide linkages (—CONH—) or peptide bonds. A peptide bond is a chemical bond formed between two molecules when the carboxyl of one molecule reacts with the amino of the other molecule, releasing a molecule of water. The resulting CO—NH bond, is called a peptide bond, and the resulting molecule is called an amide. Polyamides may occur both naturally (e.g., proteins such as wool and silk) and may be made artificially (e.g., nylons, aramids, and sodium poly(aspartate).

The term "homopolymer" refers to a natural or synthetic polymer derived from a single monomer.

The terms "polycaprotactone", 6-Caprolactone polymer, and "PCL" are used interchangeably to refer to a biodegradable polyester having the molecular formula $(C_6H_{10}O_2)_n$, and having a molecular weight of about 80,000 daltons. PCL may be obtained commercially, for example, from Sigma-Aldrich.

The terms "poly(glycolic acid)", polyglycolide, and "PGA" are used interchangeably herein to refer to a biodegradable, thermoplastic polymer and the simplest linear, aliphatic polyester. PGA may be obtained commercially, for example, from Sigma-Aldrich.

A "polylactide" is a biodegradable polymer derived from lactic acid. Poly(lactide) or PLA exists in two stereo forms, signified by a D or L for dexorotary or levorotary, or by DL for the racemic mix. The term "PLLA" refers to the biodegradable aliphatic polyester homopolymer poly L-lactic acid. PLLA may be obtained commercially, for example, from Alkermes, Inc.

The terms poly (lactic acid-glycolic acid), poly (D,L-lactide-c-glycoside), and PLGA are used interchangeably to refer to a copolymer of polylactic acid and glycolic acid. PLGA may be obtained commercially, for example, from Alkermes, Inc.

The term "poly(orthoester)" refers to a synthetic material having the molecular structure

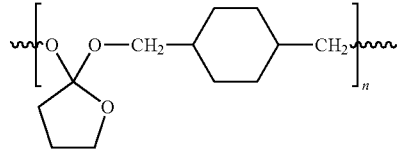

which is hydrophobic with hydrolytic linkages that are acid-sensitive, but stable to base. See J. C. Middleton, A. J. Tipton, Biomaterials 21: 2335-46 (2000).

A phosphazene is a ring or chain polymer that contains alternating phosphorus and nitrogen atoms with two substituents on each phosphorus atom such that a phosphorus atom is covalently linked to a nitrogen atom by a double bond and to three other atoms or radicals by single bonds. Two examples are hexachlorocyclotriphosphazene, a cyclic compound, whose chemical formula is more descriptively written as $(PNCl_2)_3$ and bis(triphenylphosphine)iminium chloride (PPNCl). The term "poly(phosphazene)" refers to polymers having a phosphazene repeating unit and the general structure (—RR'P=N—).

A "polysaccharide" is a long-chain natural or synthetic polymer made up of linked simple sugars (monosaccharides) such as glucose and closely related molecules. Two monosaccharide molecules may be joined by a glycosidic bond to form a disaccharide, as, for instance, in the linkage of glucose and fructose to create sucrose. More complicated polysaccharides such as starch, glycogen, cellulose or chitin consist of numerous monosaccharide units joined by glycosidic bonds.

The term "porous" as used herein relates to having minute openings, pores, or holes that may be filled (permeated) by water, air or other materials.

As used herein, the term "stem cells" refers to undifferentiated cells having high proliferative potential with the ability to self-renew that may migrate to areas of injury and may generate daughter cells that may undergo terminal differentiation into more than one distinct cell phenotype. These cells have the ability to differentiate into various cells types and thus promote the regeneration or repair of a diseased or damaged tissue of interest. The term "cellular differentiation" refers to the process by which cells acquire a cell type. The term "progenitor cell" as used herein refers to an immature cell in the bone marrow that may be isolated by growing suspensions of marrow cells in culture dishes with added growth factors. Progenitor cells are referred to as colony-forming units (CFU) or colony-forming cells (CFC). The specific lineage of a progenitor cell is indicated by a suffix, such as, but not limited to, CFU-F (fibroblastic).

As used herein, the terms "osteoprogenitor cells," "mesenchymal cells," "mesenchymal stem cells (MSC)," or "marrow stromal cells" are used interchangeably to refer to multipotent stem cells that differentiate from CFU-F cells capable of differentiating along several lineage pathways into osteoblasts, chondrocytes, myocytes and adipocytes. When referring to bone or cartilage, MSCs commonly are known as osteochondrogenic, osteogenic, chondrogenic, or osteoprogenitor cells, since a single MSC has shown the ability to differentiate into chondrocytes or osteoblasts, depending on the medium.

The term "chondrocytes" as used herein refers to cells found in cartilage that produce and maintain the cartilaginous matrix. From least to terminally differentiated, the chondrocytic lineage is (i) Colony-forming unit-fibroblast (CFU-F); (ii) mesenchymal stem cell/marrow stromal cell (MSC); (3) chondrocyte. The term "chondrogenesis" refers to the formation of new cartilage from cartilage forming or chondrocompetent cells.

The term "osteoblasts" as used herein refers to cells that arise when osteoprogenitor cells or mesenchymal cells, which are located near all bony surfaces and within the bone marrow, differentiate under the influence of growth factors. Osteoblasts, which are responsible for bone matrix synthesis, secrete a collagen rich ground substance essential for later mineralization of hydroxyapatite and other crystals. The collagen strands to form osteoids: spiral fibers of bone matrix. Osteoblasts cause calcium salts and phosphorus to precipitate from the blood, which bond with the newly formed osteoid to mineralize the bone tissue. Once osteoblasts become trapped in the matrix they secrete, they become osteocytes. From least to terminally differentiated, the osteocyte lineage is (i) Colony-forming unit-fibroblast (CFU-F); (ii) mesenchymal stem cell I marrow stromal cell (MSC); (3) osteoblast; (4) osteocyte. The term "osteogenesis" refers to the formation of new bone from bone forming or osteocompetent cells.

Although the lineage of adipocytes is still unclear, it appears that MSCs may differentiate into two types of lipoblasts, one that give rise to white adipocytes and the other to brown adipocytes. Both types of adipocytes store fat.

Unless defined otherwise, all technical and scientific terms used herein have the same meaning as commonly understood by one of ordinary skill in the art to which this invention belongs. Although any methods and materials similar or equivalent to those described herein also may be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

Example 1

The Fabrication of Tissue Engineering Scaffolds

The Electrospinning Process

Electrospinning is a fiber forming technique that relies on charge separation to produce nano- to microscale fibers, which typically form a non-woven matrix. The terms "non-woven matrix", "nonwoven mesh" or "nonwoven scaffold" are used interchangeably herein to refer to a material comprising a randomly interlaced fibrous web of fibers. Generally, individual electrospun fibers have large surface-to-volume and high aspect ratios resulting from the smallness of their diameters. These beneficial properties of the individual fibers are further enhanced by the porous structure of the non-woven fabric, which allows for cell infiltration, cell aggregation, and tissue formation.

The electrospinning process is affected by varying the electric potential, flow rate, solution concentration, capillary-collector distance, diameter of the needle, and ambient parameters like temperature. Therefore, it is possible to manipulate the porosity, surface area, fineness and uniformity, diameter of fibers, and the pattern thickness of the matrix.

While the following is a description of a preferred embodiment, the present invention includes other protocols that achieve the same results.

One nonlimiting example of an apparatus and method used for electrospinning has been disclosed in U.S. application Ser. No. 11/291,701, which is incorporated herein by reference in its entirety. FIG. 1 is a diagrammatic representation of the electrospinning setup used herein, which is comprised of a syringe pump containing a 20 gauge needle. The syringe pump was mounted on a robotic arm in order to control the splaying of fibers on the collector. An electrically grounded stainless steel plate of dimensions 15 cm×30 cm was used as the collector. The syringe pump was filled with the polymer-ceramic solution, and a constant flow rate of 0.10 ml/min was maintained using the syringe pump. The positive output lead of a high voltage power supply (Gamma High Voltage, inc.) was attached to the needle, and a 17 kvolt voltage was applied to the solution. The collector-to-needle distance was 15 cm. When the charge of the polymer at increasing voltage exceeded the surface tension at the tip of the needle, the polymer splayed randomly as fibers. These were collected as nonwoven mats on the grounded plate.

This electrospinning technique is used to prepare a fibrous matrix comprising a ceramic-polymer composite according to the present invention. The term "composite" as used herein refers to a complex material, in which two or more distinct substances combine to produce structural or functional properties not present in any individual component. The composite of the present invention is created by combining a bioactive ceramic component with a polymer component.

The polymer component may be any natural or synthetic biocompatible polymer that may be dissolved in an organic (meaning carbon-containing) solvent for electrospinning according to the present invention. While any solvent generally useful to prepare a polymer solution may be used for this purpose, the fiber size, pore size, and polymer structure of the ceramic-polymer mats formed according to the present invention are determined by the solvent used to form the ceramic-polymer mats. Examples of suitable solvents include, but are not limited to, dimethylsulfoxide (DMSO), ethyl acetate, benzene, 2-butanone, carbon tetrachloride, n-heptane, n-hexane, n-pentane, methylene chloride, dimethylformamide, chloroform, formic acid, ethyl formate, acetic acid, hexafluoroisopropanol, cyclic ethers, acetone, $C_2$-$C_5$ alcohol acetates, 1-4 dioxane, and combinations thereof. In some embodiments, the solvent is selected to be noncytotoxic.

A solution generally is considered as a homogeneous mixture of two or more substances; it is frequently, though not necessarily, a liquid. In a solution, the molecules of the solute (or dissolved substance) are uniformly distributed among those of the solvent. A suspension is a dispersion (mixture) in which a finely-divided species is combined with another species, with the former being so finely divided and mixed that it doesn't rapidly settle out. In everyday life, the most common suspensions are those of solids in liquid water.

Examples of polymers that may be incorporated into the composite of the present invention include, without limitation, nondegradable polymers (such as polyurethanes (meaning a thermoplastic polymer produced by the reaction of polyisocyanates with linear polyesters or polyethers containing hydroxyl groups), polyvinylidine fluoride (($-H_2C=CF_2-)_n$), and polyvinylidine fluoride trifluoroethylene) and degradable polymers (such as poly(lactic acid-glycolic acid), poly(lactic acid), poly(glycolic acid), a poly(orthoester), a poly(phosphazene), poly(caprolactone), a polyacrylamide, and collagen.

As used herein, the term "bioactive ceramic" includes, but is not limited to, such substances as hydroxyapatite, tricalcium phosphate and bioactive glasses, each of which has superior osteoconductive properties. There are several calcium phosphate ceramics that are considered biocompatible. Some of these materials include, in order of solubility, tetracalcium phosphate $(Ca_4P_2O_9)$>amorphous calcium phosphate>alpha-tricalcium phosphate $(Ca_3(PO_4)_2$>beta-tricalcium phosphate ("β-TCP") $(Ca_3PO_4)_2$>>hydroxyapatite $(Ca_{10}(PO_4)_6(OH)_2)$.

The terms "hydroxylapatite", "hydroxyapatite" and "HA" are used interchangeably to refer to a mineral that is the major constituent of bone and tooth mineral. It is a finely divided, crystalline, nonstoichiometric material rich in surface ions (including carbonate, magnesium, and citrate ions). It is thermodynamically stable at physiological pH (meaning it does not break down under physiological conditions) and may form strong chemical bonds with surrounding bone.

In some embodiments, electrospun composites according to the present invention contain about 10% to about 40% by weight of a ceramic component and about 60% to about 90% by weight of a polymer. In some embodiments, the electrospun composites contain at least 10%, at least 15%, at least 20%, at least 25%, at least 30%, at least 35%, or at least 40% by weight of a ceramic component. In some embodiments, the electrospun composites contain no more than 40%, no more than 35%, no more than 30%, no more than 25%, no more than 20%, no more than 15%, or no more than 10% by weight of a ceramic component. In some embodiments, the electrospun composites contain at least 60%, at least 65%, at least 70%, at least 75%, at least 80%, at least 85%, or at least 90% of a polymer. In some embodiments, the electrospun composites contain no more than 90%, no more than 85%, no more than 80%, no more than 75%, no more than 70%, no more than 65%, or no more than 60% by weight of a polymer.

According to some embodiments of the present invention, the bioactive ceramic component of the composite comprises both hydroxyapatite and tricalcium phosphate. See, Wutticharoenmongkol P et al. J Nanosci Nanotechnol. (2006) 6(2): 514-522; Thomas V et al. J Nanosci Nanotechnol. (2006). 6(2): 487-493. According to some such embodiments, the composite comprises two calcium phosphate ceramics for each polymer. According to one embodiment of the present invention, a composition of bioactive ceramics comprising 20% hydroxyapatite:80% beta-tricalcium phosphate ("20/80 HA/β-TCP") is combined with a polymer, such as polycaprolactone (PCL), and electrospun. Bioactive ceramic compositions comprising 20/80 HA/β-TCP have been shown to promote stem cell differentiation into osteoblasts (Livingston Arinzeh, T. L., Tran, T., McAlary, J., Dalcusi, G. 2005. *Comparative osteogenic activity of various calcium phosphate ceramic compositions in vitro and in vivo*. Biomaterials. 26(17), pp. 3631-3638)). 20/80 HA/β-TCP also strikes an optimal balance between supporting bone formation while degrading existing bone to allow for bone replacement.

The solution of polymer is prepared by weighing the required amount of polymer and dissolving it in a volume of solvent. In one embodiment, methylene chloride is used as the solvent. In another embodiment, methylene chloride and dimethylformamide in the ratio of 80:20 was used as the solvent.

The concentration of the final solution depends on the concentration that is required. In some embodiments, for example, methylene chloride is used as the solvent. In one such embodiment, 10 ml of methylene chloride (density is 1.3255 g/cm$^3$) is used to dissolve 1 g of polymer. In another embodiment, 10 ml of methylene chloride is used to dissolve 2 g of polymer. In another embodiment, 10 ml of methylene chloride is used to dissolve 0.5 g of polymer. In another embodiment, 10 ml of methylene chloride is used to dissolve 1.5 g of polymer.

The solution is stirred using a magnetic stirrer overnight at room temperature. To make a composite material of polymer and ceramic, the required amount of ceramic is weighed and added to the polymer solution in a beaker. Hydroxyapatite having an average particle diameter of about 100 nm and β-TCP having an average particle diameter of about 100 nm, may be purchased from Berkeley Advanced Biomaterials. The mixture is stirred manually using a glass stirrer for a few minutes and then poured into the syringe for electrospinning. The organic solvent substantially evaporates during the electrospinning process, resulting in less than about 1% of the solvent remaining in the final product.

Composites having ceramic loadings from about 10% to about 50% by weight were fabricated. For example, a 20/80 HA/TCP polymer composite is prepared by preparing the required amount of the ceramic component and then adding it to the polymer solution. The ceramic component is prepared by mixing 20 weight percent HA and 80 weight percent of βTCP. The required amount of the ceramic component is added to 10 ml of the polymer solution and stirred for a few minutes prior to loading the composite into the syringe for electrospinning.

The bioactive ceramic-polymer composite of the present invention produces a fibrous mat that has micron sized fiber diameters and micron sized pore diameters. This increase in fiber and pore diameter size from the nano sized fibers to the micron sized fibers improves cell infiltration, aggregation, and tissue formation throughout the scaffold, making it optimal for tissue engineering. In some such embodiments, the microscale fibers have a diameter ranging from about 1 micrometer to about 50 micrometers. In some embodiments, the diameter of the microfibers averaged from about 1 micrometer to about 5 micrometers.

Morphology and Elemental Analysis

The morphology of the electrospun mats was studied using LEO 1530 scanning electron microscopy (SEM). The estimate of fiber size of electrospun scaffolds was determined from the SEM images using ImageJ software. SEM-EDXA was performed on the sample to confirm the presence of calcium and phosphorous in the electrospun mats. Mapping for calcium was performed on the electrospun sample to determine the distribution of the ceramic in the polymer mat. An accelerating voltage of 10 KV voltage and a working distance of 10 mm were used for the SEM EDXA and mapping analysis.

Energy Dispersive X-ray Spectroscopy (EDS) is an analytical technique that utilizes an electron beam to impact on the sample. This produces x-rays that are characteristic of the elements found on the sample. EDS may be coupled with several applications, including Scanning Electron Microscopy (SEM), Transmission Electron Microscopy (TEM) and Scanning Transmission Electron Microscopy (STEM).

Figure 2A:
FIG. 2A shows a scanning electron micrograph of one embodiment of an electrospun polycaprolactone containing 10% nanohydroxyapatite.
Figure 2B:
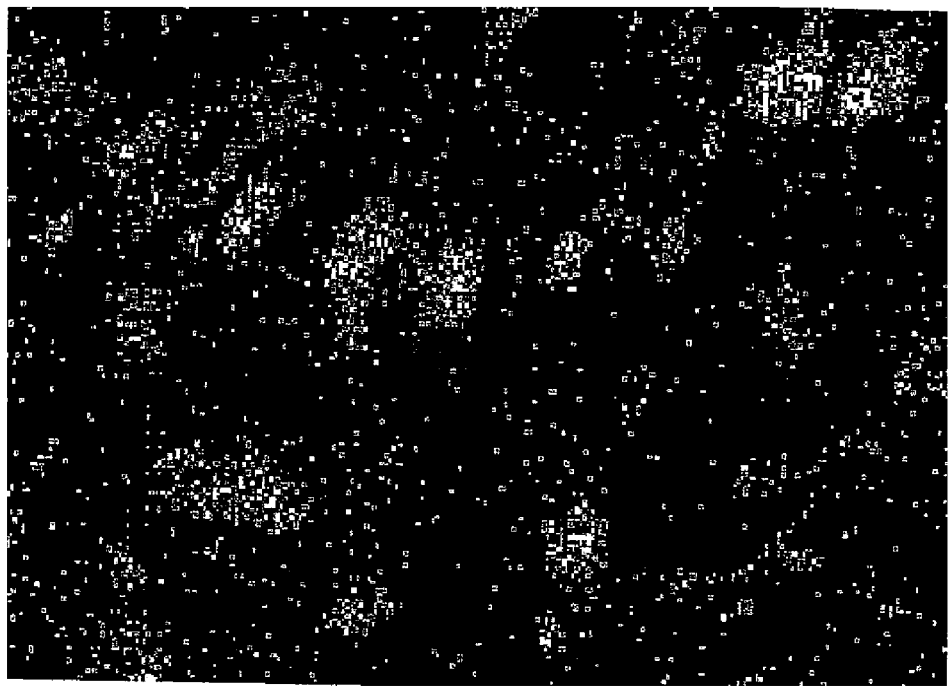
FIG. 2B shows corresponding energy dispersive x-ray mapping of calcium levels of the mat shown in FIG. 2A as an indicator of the location of hydroxyapatite.

FIG. 2b shows an energy-dispersive x-ray map of the fibers shown in FIG. 2a. The location of the hydroxyapatite may be identified by the calcium levels in the energy-dispersive x-ray map. The EDX spectrum results confirmed the presence of calcium and phosphorous in the electrospun mats.

Figure 3A:
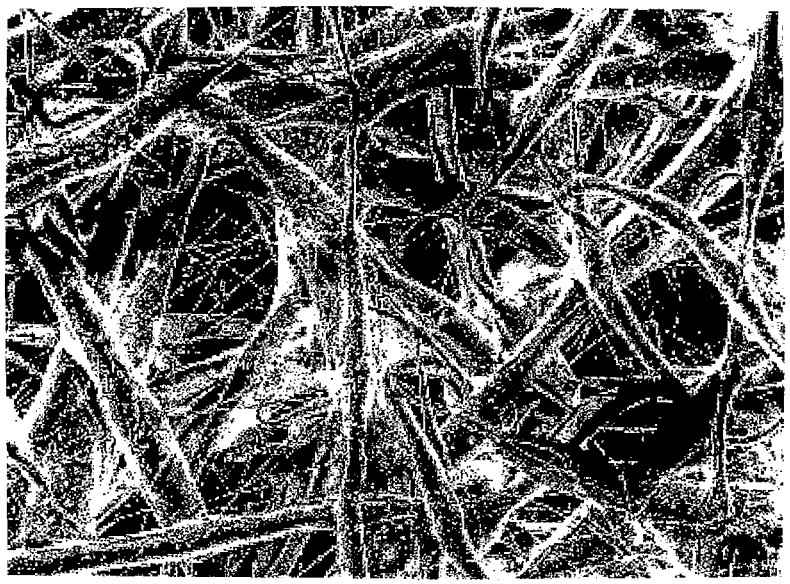
FIG. 3A shows a scanning electron micrograph of one embodiment of an electrospun mat containing 30% HA-TCP formed using methylene chloride as solvent.
Figure 3B:
FIG. 3B shows corresponding energy dispersive x-ray mapping of calcium levels of the mat shown in FIG. 3A as an indicator of the location of hydroxyapatite.

FIG. 3A shows a scanning electron micrograph of one embodiment of an electrospun mat containing 30% HA-TCP using methylene chloride as solvent. FIG. 3B shows corresponding energy dispersive x-ray mapping of calcium levels of the mat shown in FIG. 3A as an indicator of the location of hydroxyapatite. The SEM shows that there were smaller diameter fibers forming a web-like network in between larger diameter fibers. The larger diameter fibers were micron scale with average diameter increasing from about 20 microns to 50 microns with the increase in ceramic concentration, while the smaller diameter fibers were in nanometer range. The inter-fiber space between large size fibers is around 100 microns. Calcium mapping results obtained by SEM-EDX showed that the ceramic was uniformly distributed in the mat (the mapping was stopped after 30 minutes as the data were sufficient for this purpose).

Figure 4A:
FIG. 4A shows a scanning electron micrograph of one embodiment of an electrospun mat containing 30% HA-TCP formed using methylene chloride and dimethylformamide as solvent.
Figure 4B:
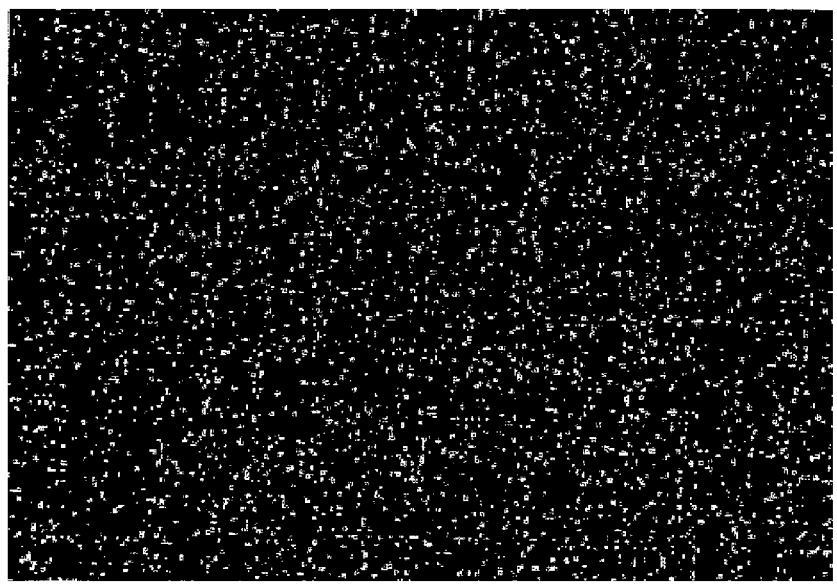
FIG. 4B shows corresponding energy dispersive x-ray mapping of calcium levels of the mat shown in FIG. 4A as an indicator of the location of hydroxyapatite.

FIG. 4A shows a scanning electron micrograph of one embodiment of an electrospun mat containing 30% HA-TCP formed using methylene chloride and dimethylformamide as solvent. FIG. 4B shows corresponding energy dispersive x-ray mapping of calcium levels of the mat shown in FIG. 4A as an indicator of the location of hydroxyapatite. Calcium mapping results obtained by SEM-EDX for these 30% (HA/β-TCP)-PCL electrospun mats showed that the ceramic was uniformly distributed in the mat (the mapping was stopped after 90 minutes as the data was sufficient to assess that ceramic was uniformly distributed).

The fiber size and inter fiber size distance details for electrospun mats fabricated using methylene chloride (MC) as solvent and methylene chloride (MC) and dimethyl formamide (DMF) as solvent are shown in Table 1 and Table 2 respectively.

TABLE 1

Fiber size and inter fiber size details of electrospun mats fabricated using MC solvent (Procedure I)

|  | 10% HA-TCP | 20% HA-TCP | 30% HA-TCP | 40% HA-TCP | 50% HA-TCP |
| --- | --- | --- | --- | --- | --- |
| Fiber Diameter (μm) | 21.87 ± 5.97 | 23.72 ± 6.92 | 28.49 ± 8.94 | 45.69 ± 17.26 | 47.14 ± 14.30 |
| Inter fiber distance (μm) | 93.56 ± 30.53 | 117.06 ± 43.6 | 149.76 ± 40.28 | 156.12 ± 67.37 | 141.97 ± 51.73 |

Non-woven mats may be electrospun with ceramic loading up to 50% by weight using methylene chloride as solvent according to the present invention.

FIG. 2A shows a scanning electron micrograph of one embodiment of an electrospun polycaprolactone containing 10% nanohydroxyapatite formed using methylene chloride as solvent Fiber diameters were about 1 micron to about 5 microns and pore sizes were at least about 20 microns in diameter.

The fiber diameter and inter fiber distance details of fibers formed using methylene chloride: dimethylformamide in the ratio of 80:20 are shown in Table 2. The fibers were mostly uniform up to about 30% ceramic loading, but significant agglomerates of the ceramic started were observed to form from about 40% ceramic loading. The diameter of the fibers was significantly decreased in Procedure II compared to procedure Procedure I. There was a slight increase in the diameter of the fiber as the ceramic loading increased. Fibers were of uniform size in procedure Procedure II mats.

TABLE 2

Fiber size and inter fiber size details of electrospun
mats fabricated using MC and DMF solvent (Procedure II)

|  | 0% HA-TCP | 10% HA-TCP | 20% HA-TCP | 30% HA-TCP |
|---|---|---|---|---|
| Fiber Diameter (μm) | 2.00 ± .37 | 2.14 ± .35 | 2.23 ± .42 | 2.46 ± .75 |
| Inter fiber space ((μm)) | 14.28 ± 5.62 | 16.8 ± 2.87 | 18.90 ± .02 | 21.09 ± 5.46 |

Thermogravimetric Analysis

Thermogravimetric analysis (TGA, TA Q50) was used to obtain quantitative information as to the amount of ceramic present in the scaffold as well as confirmation that there was no solvent in the electrospun mat. The thermogravimetric analyzer measures the amount and rate of weight change in a material as a function of temperature in a controlled atmosphere. A heating rate of 10° C. per minute and maximum temperature of 500° C. was used for this study. Before 500° C., the PCL in the sample is expected to completely degrade. The remaining weight will be the ceramic.

Figure 5:
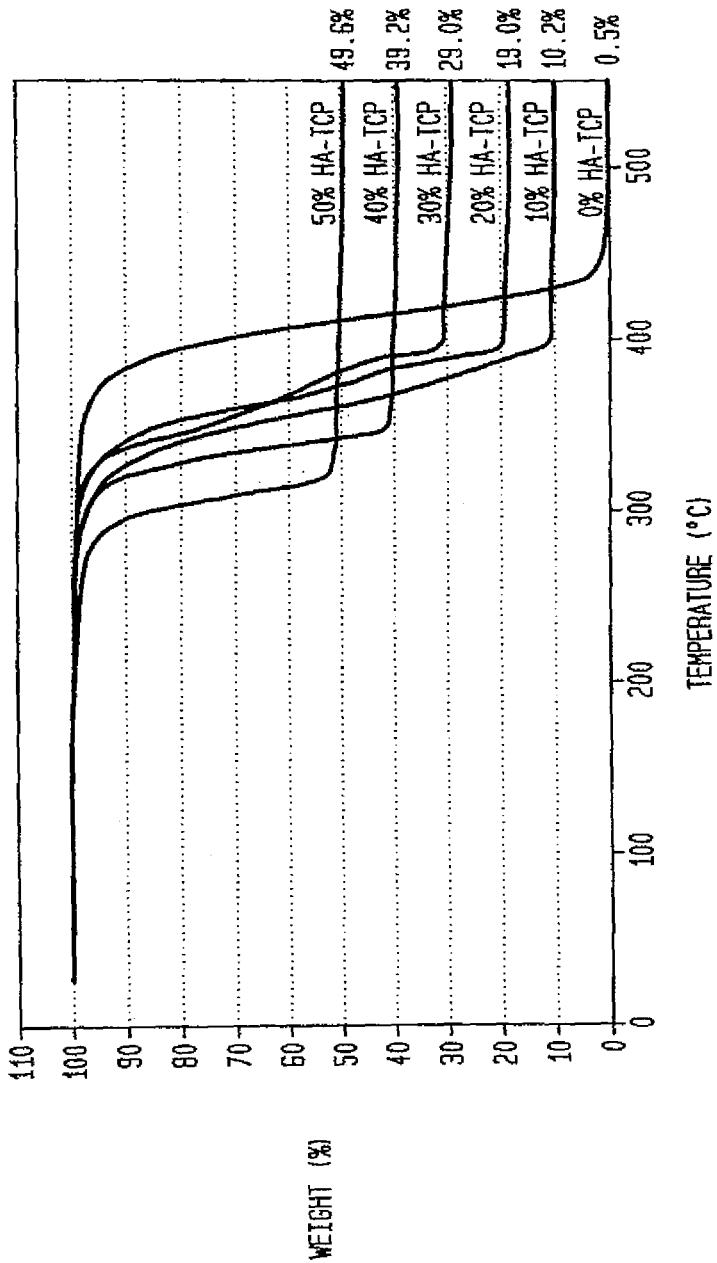
FIG. 5 shows a thermogravimetric analysis of electrospun samples made using dimethylformamide and methylene chloride as solvent (Procedure II).

The thermogravimetric analysis (TGA) profile of the 20/80 HA/TCP-PCL electrospun scaffolds fabricated using Procedure II is shown in FIG. 5. The data shown on the right axis is the weight percentage of material remaining at high temperature. The results showed that there is no substantial level of solvent left in the electrospun scaffolds. The PCL likely is degraded fully before 500° C., and this data confirms that the weight percentage remaining at that temperature is approximately the amount of ceramic added to the starting solution. As the sample was selected randomly for testing, the data also suggests that the ceramic is uniformly dispersed throughout the mat. The profile of the weight loss also shows that the pure PCL mat degrades at a higher temperature than scaffolds containing ceramic and as the ceramic concentration increases, the material degrades at a progressively lower temperatures. This suggests that the thermal degradation of PCL electrospun mats is being catalyzed by ceramic.

Figure 6:
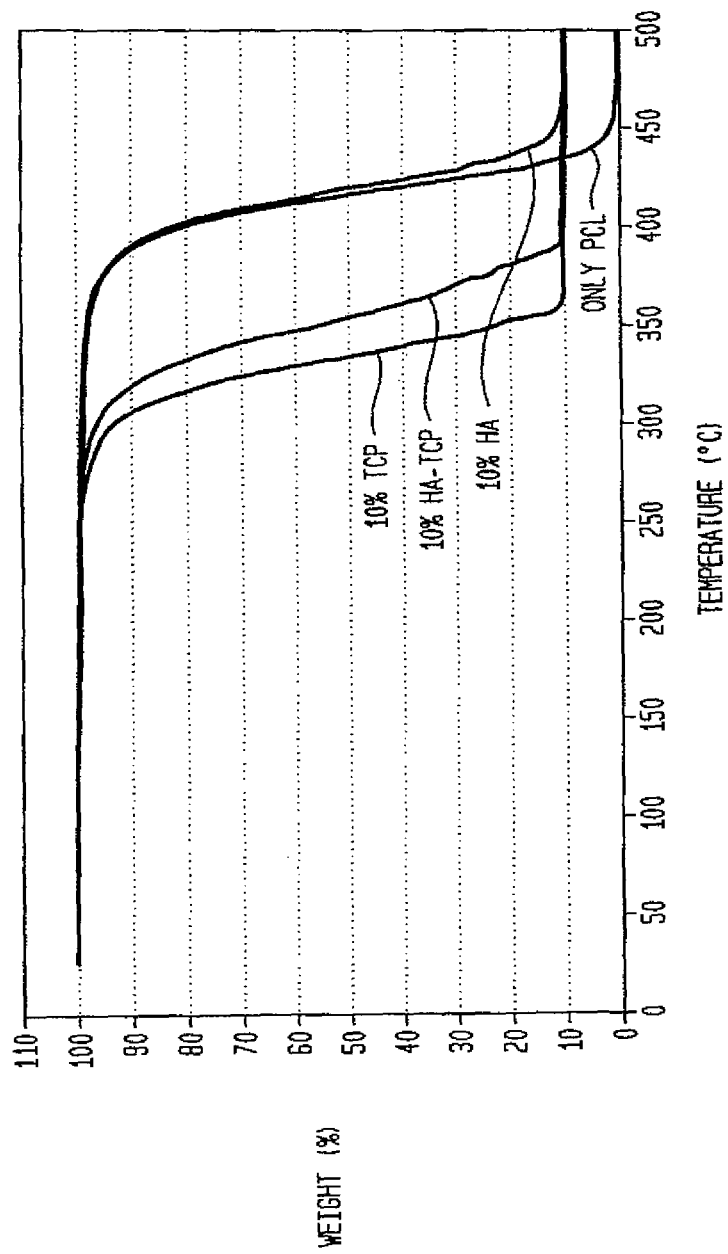
FIG. 6 shows a thermogravimetric degradation profile of electrospun samples formed using dimethylformamide and methylene chloride as solvent (Procedure II).

In order to better understand this behavior, the thermal degradation profile of only HA electrospun composite (10%), only β-TCP electrospun composite (10%) and 20HA/80β-TCP electrospun composite (10%) were compared to degradation of PCL-only electrospun mats. FIG. 6 shows a thermogravimetric degradation profile of electrospun samples made using dimethylformamide and methylene chloride as solvent (Procedure II). FIG. 6 shows that β-TCP accelerates the thermal degradation of the HA/TCP mat and not HA. Similar behavior also was observed in mats formed under Procedure I. Without being limited by theory, β-TCP also may accelerate the degradation of PCL electrospun composite under hydrolytic conditions.

Differential Scanning Calorimeter (DSC)

(1) Crystallization Behavior

Figure 7:
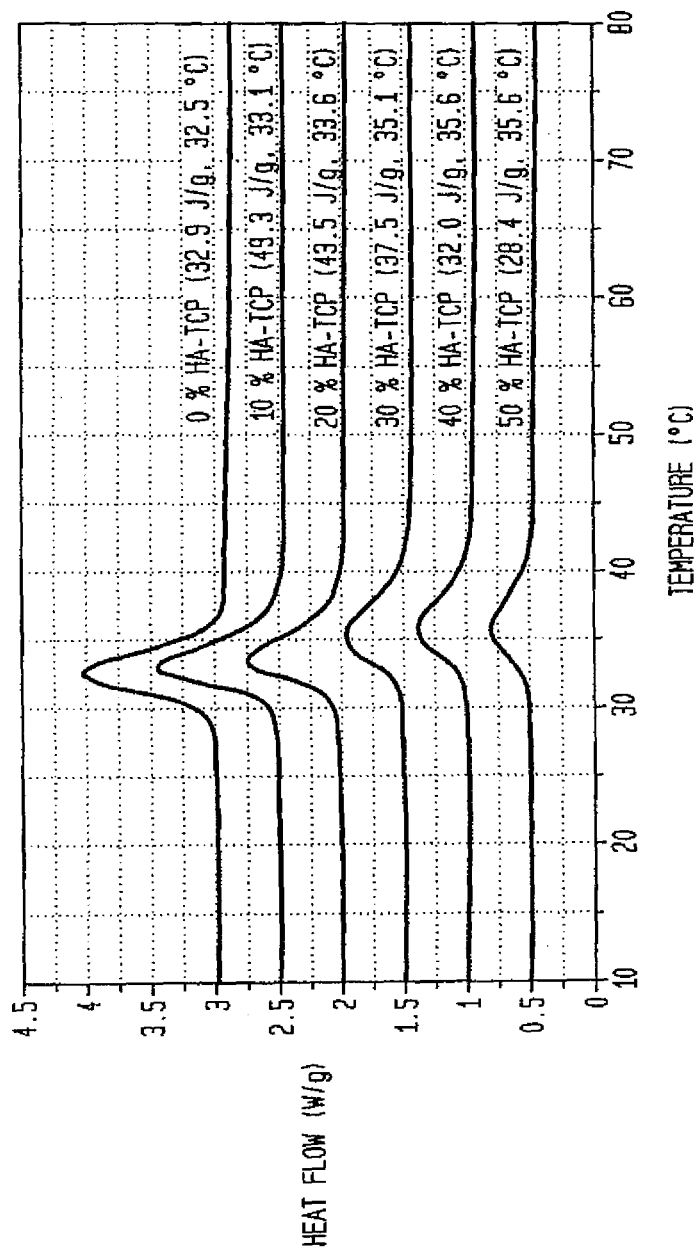
FIG. 7 shows the crystallization behavior of electrospun composites formed using methylene chloride (MC) as solvent. The heat of fusion ($H_f$) for crystallization and crystallization temperature values are labeled on the graphs.
Figure 8:
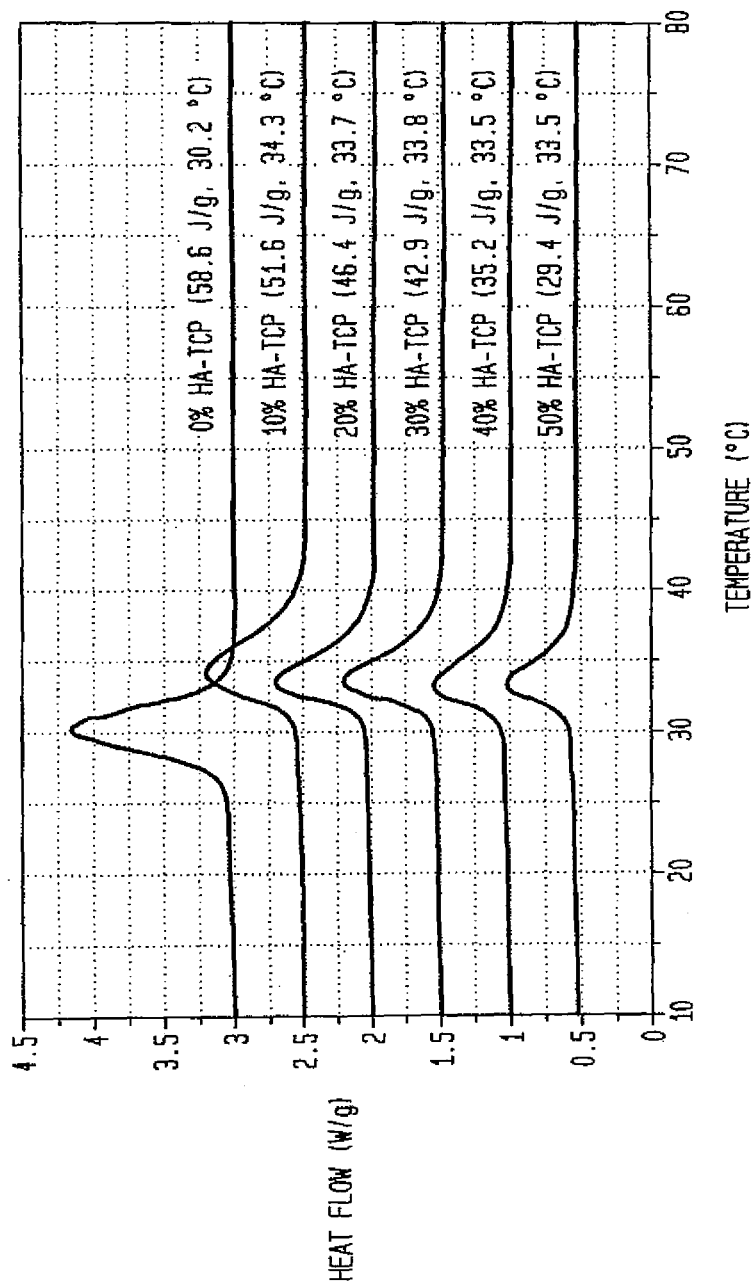
FIG. 8 shows the crystallization behavior of electrospun composites formed using methylene chloride (MC) and dimethylformamide (DMF) as solvent (Procedure II). The heat of fusion ($H_f$) for crystallization and crystallization temperature values are labeled on the graphs.

FIG. 7 shows the crystallization behavior of electrospun composites formed using methylene chloride (MC) as solvent and FIG. 8 shows the crystallization behavior of electrospun composites formed using methylene chloride (MC) and dimethylformamide (DMF) as solvent (Procedure II). The heat of fusion ($H_f$) for crystallization and crystallization temperature values are labeled on the graphs. As shown in FIG. 7, the crystallization temperature (Tc) increased with the addition of the ceramic. The increase of Tc indicates that the nanoceramics acted as a nucleating agent. This effect was more prominent for the Procedure I mats (FIG. 7) than for the Procedure II mats (FIG. 8). The nucleating effect appears to be reduced slightly with the increase in the ceramic concentration incase of Procedure I mats, whereas the nucleating effect was increased slightly in the case of Procedure II mats until 30% concentration was reached. Because it has been shown that uniform dispersion of the ceramic in a composite is necessary for the ceramic to act as a nucleating agent [Jiann-Wen Huang. *Isothermal crystallization of high-density polyethylene and nanoscale calcium carbonate composites* J of applied polymer science. 2007; 107: 3163-3172], these observations suggest that the uniformity of the ceramic is reduced slightly in the case of mats fabricated using Procedure I, whereas the uniformity of the ceramic is not affected in case of mats fabricated using Procedure II until 30% ceramic concentration is reached.

A decrease in the heat of fusion required was observed for crystallization as the concentration of ceramic increased (values shown on the graph, FIG. 8), which may be related to the concentration of PCL present in the composites. As indicated in Table 3, the rate of crystallization decreased with the addition of ceramic. Without being limited by theory, the reduction in the crystallization rate may take place because the interaction between the particles and polymer may retard molecular mobility. This, in turn, may retard the crystallization rate [Tamaki Miyazaki, Sumie Yoshioka, Yukio Aso, Tom Kawanishi. *Crystallization rate of amorphous nifedipine analogues unrelated to the glass transition temperature*. Int'l J. Pharmaceutics. 2007; 336:191-195; Li Sun, Jin-Tao Yang, Gen-Yao Lin, Ming-Qiang Zhong. *Crystallization and thermal properties of polyamide 6 composites filled with different nanofillers*. Materials Letters. 2007; 61: 3963-3966; Sha-Ni Lia, Zhong-Ming Lia, Ming-Bo Yanga, Zong-Qian Hua, Xiang-Bin Xua, Rui Huanga. *Carbon nanotubes induced nonisothermal crystallization of ethylene-vinyl acetate copolymer*. Materials Letters. 2004; 58:3967-3970].

TABLE 3

Data of glass transition, crystallization rate
and crystallinity of electrospun composites

|  | Tg (MC) °C. | Tg (MC + DMF) °C. | Crystallization time (tc) (MC) (min$^{-1}$) | Crystallization time (tc) (MC + DMF) (min$^{-1}$) | Crystallinity (%) (MC) | Crystallinity (%) (MC + DMF) |
|---|---|---|---|---|---|---|
| Only PCL | -53.7 | -54.0 | 0.80 | 0.79 | 43.5% | 40.6% |
| 10% HT | -52.0 | -52.8 | 0.46 | 0.56 | 43.5% | 42.0% |
| 15% HT | — | -51.0 | — | 0.52 | — | — |
| 20% HT | -49.8 | -47.5 | 0.43 | 0.50 | 44.3% | 42.0% |

TABLE 3-continued

Data of glass transition, crystallization rate
and crystallinity of electrospun composites

| | Tg (MC) °C. | Tg (MC + DMF) °C. | Crystallization time (tc) (MC) (min$^{-1}$) | Crystallization time (tc) (MC + DMF) (min$^{-1}$) | Crystallinity (%) (MC) | Crystallinity (%) (MC + DMF) |
|---|---|---|---|---|---|---|
| 25% HT | — | −44.0 | — | 0.44 | — | — |
| 30% HT | −43.4 | −47.6 | 0.41 | 0.46 | 45.0% | 43.4% |
| 40% HT | −44.2 | −52.8 | .46 | 0.47 | 45.5% | 43.5% |
| 50% HT | −54.4 | −53.8 | .54 | 0.49 | 44.8% | 42.6% |

(2) Melting Behavior

Figure 9:
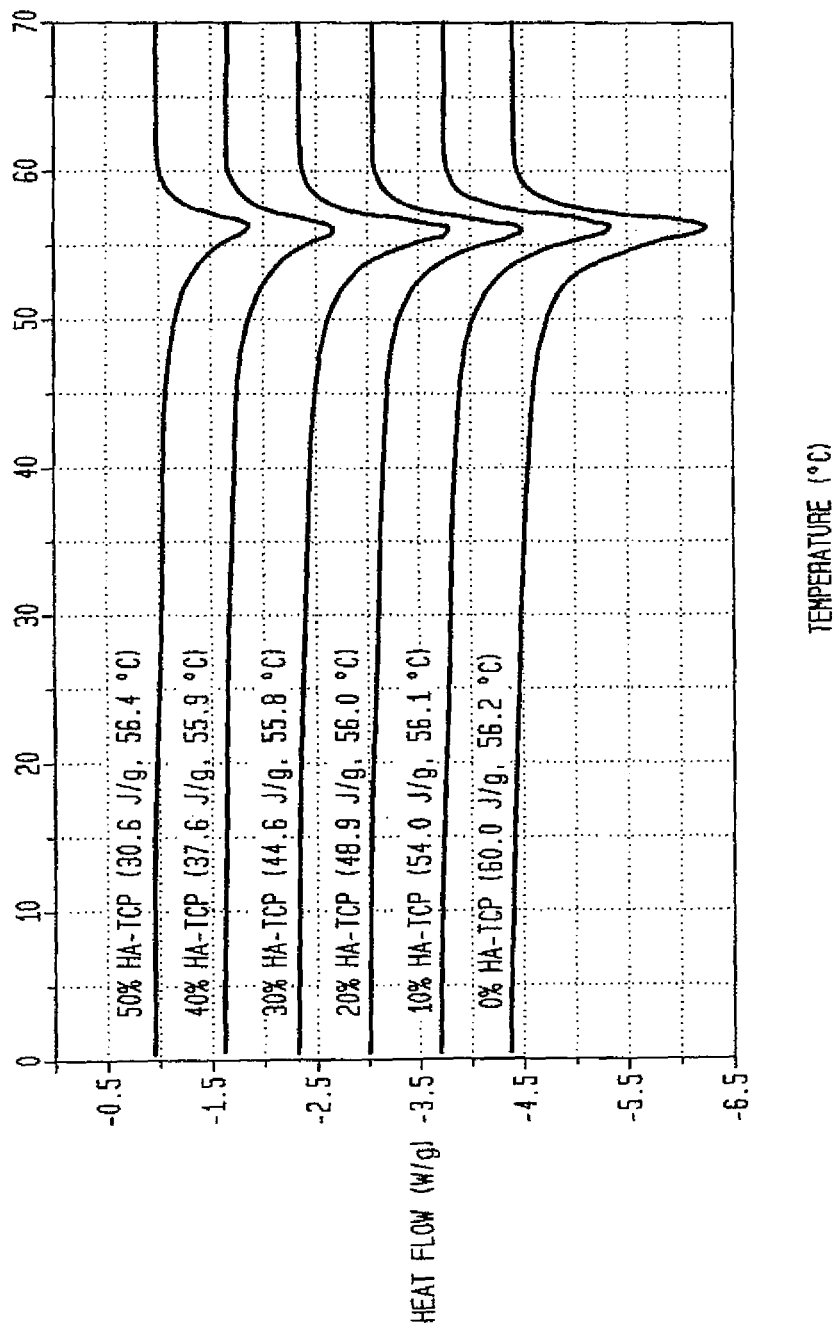
FIG. 9 shows the melting behavior of electrospun composites formed using methylene chloride as solvent. (Procedure I). The heat of fusion ($H_f$) for crystallization and crystallization temperature values are labeled on the graphs.
Figure 10:
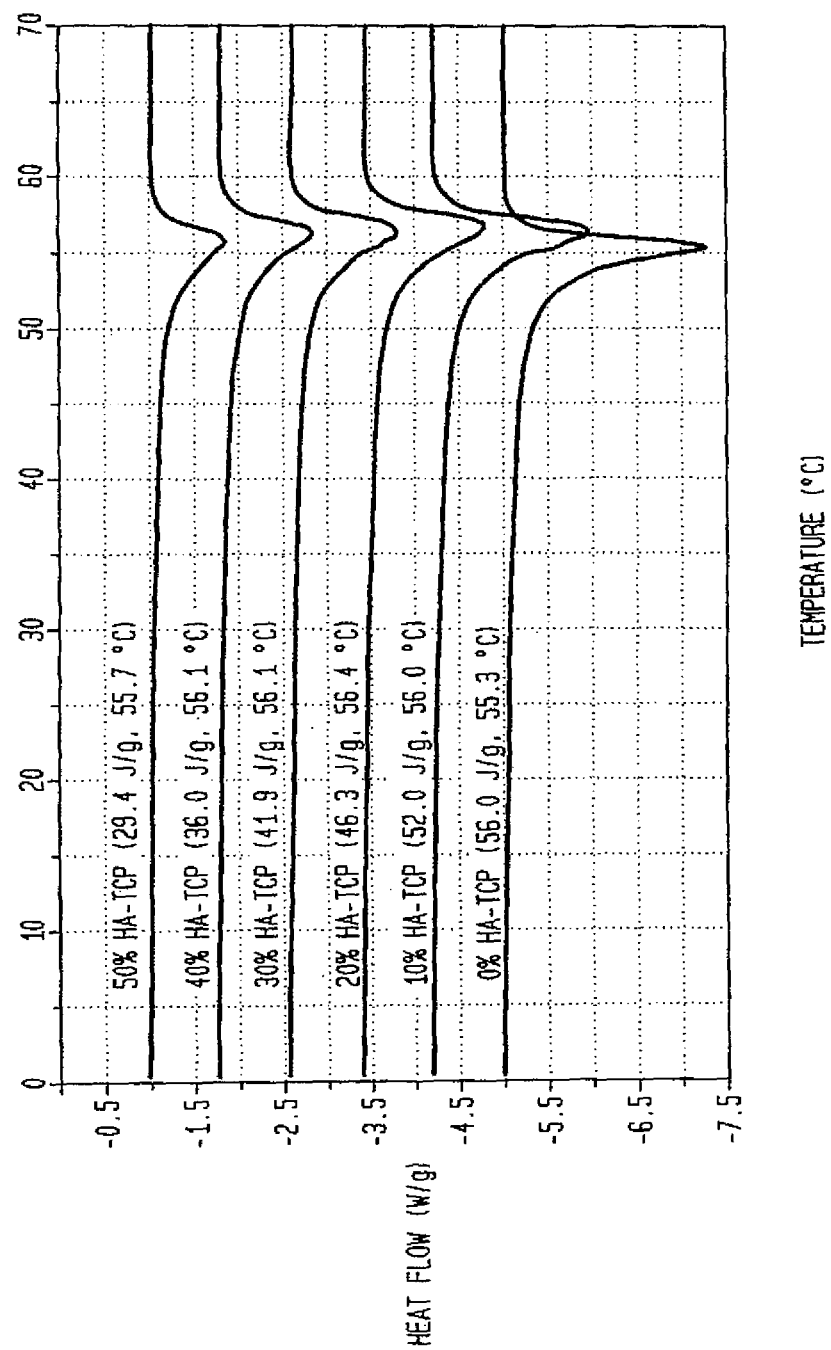
FIG. 10 shows the melting behavior of electrospun composites formed using methylene chloride (MC) and dimethylformamide (DMF) as solvent (Procedure II). The heat of fusion ($H_f$) for crystallization and crystallization temperature values are labeled on the graphs.

FIG. 9 shows the melting behavior of electrospun composites formed using methylene chloride as solvent. (Procedure I), and FIG. 10 shows the melting behavior of electrospun composites formed using methylene chloride and dimethylformamide as solvent (Procedure II). The heat of fusion ($H_f$) for crystallization and crystallization temperature values are labeled on the graphs.

Based on these data, the melting point of PCL electrospun mat has been estimated to be 56° C. There was a slight increase in the melting point of composites prepared according to Procedure I and Procedure II compared to PCL alone, which suggests that the crystal size of PCL is not affected by the ceramic. However, there is a significant decrease in the heat of fusion required for melting as the concentration of ceramic increased, which may be related to the weight percentage of polymer in the composite.

The crystallinity of the electrospun scaffolds was calculated from their heat of fusion for melting values. The 100% crystallinity value of PCL used for calculating the crystallinity of the mats is 138 KJ/g. There is a slight increase in the crystallinity of the samples with the increase in the ceramic concentration when corrected for the weight of the ceramic. Also, the crystallinity of mats fabricated using MC (Procedure I) is slightly more crystalline than mats fabricated using MC and DMF (Procedure II) (Table 3).

Thermally Stimulated Current

As the glass transition (Tg) of PCL was not visible using DSC technique, a highly sensitive technique thermally stimulated current (TSC) technique was used to determine the glass transition. The Tg value of only PCL electrospun mat was found to be −54° C. [Table 3]. In the case of composites fabricated using Procedure I, the glass transition values of the composites increased with the increase in ceramic concentration up to 30% ceramic level, and started to decrease with further increase in the ceramic level, where as in case of mats fabricated using Procedure II, the Tg values increased till up to 25% ceramic concentration level and started to decrease with further increase in ceramic level. There is a maximum increase of about 10° C. in the glass transition values of electrospun composite compared to the pure PCL mat.

Porosity and Pore size

The porosity of the samples was determined from their measured density values and their pore size was determined using the mercury porosimetry. The density of the electrospun mat (Dmat) was calculated by weighing ten samples from each mat. The density values given by manufactures for PCL pellet is 1.14 gm/cm$^3$ and HA and β-TCP are 3.16 gm/cm$^3$ and 3.06 gm/cm$^3$. The density of the raw material based on the composition used was calculated using the formula: Draw=1/((conc. of ceramic/ρceramic)+(conc. of PCL/ρPCL). The porosity was calculated using the formula: porosity (%)=(1−Dmat/Draw)*100 [Guobao Wei, Peter Ma. Structural and properties of nano-hydroxyapatite/polymer composite scaffolds for bone tissue engineering. Biomaterials. 2004; 25: 4749-4757].

The porosity of the MC and MC+DMF electrospun composites is around 78%, and there is no correlation observed in the loading of the ceramic and porosity. However, the mats using MC and the mats made using MC+DMF were highly differing in the pore size, which was determined using mercury porosimetry. The mean pore size of a pure PCL mat is about 2.5 microns, 30% HA-TCP composite made using MC is about 80.0 microns, and 30% HA-TCP composite made using MC+DMF is 7.0 microns.

Example 2

Incorporation of Stem Cells into a Ceramic-Polymer Matrix of the Present Invention In some embodiments, osteoblasts or mesenchymal stem cells are incorporated into the ceramic-polymer scaffold. In some such embodiments, the electrospun ceramic-polymer matrix is a scaffold for tissue engineering in vivo. In some such embodiments, the electrospun ceramic-polymer matrix provides a culturing medium in vitro.

Cell Proliferation

Human MSCs are isolated from adult, human whole bone marrow according to standard techniques and are seeded onto the ceramic-polymer scaffolds of the present invention and grown in standard growth medium (DMEM, 10% fetal bovine serum, 1% antibiotic/antimycotic) for 14 days. Cell proliferation is assessed using Vybrant's MTT Cell Proliferation Assay Kit (Molecular Probes, Inc.).

Osteogenic Differentiation.

Bioactive ceramic-polymer scaffolds are created by the process of electrospinning, and human mesenchymal stem cells are grown on the scaffolds to determine whether the scaffolds support osteogenic differentiation.

hMSCs are grown in control medium (DMEM, 10% FBS, 1% antibiotic) or osteogenic inducing medium (OS) (Control medium with 100 nM dexamethasone, 10 mM b-glycerophosphate, 0.05 mM L-ascorbic acid-2-phosphate) on bioactive ceramic-polymer scaffolds created by electrospinning.

On the day of cell seeding, scaffolds are soaked first in 100% ethanol for 20 minutes, and then three times in PBS, 20 minutes each, for sterilization. Scaffolds then are placed into assigned wells of a 96-well microtiter plate (B-D Falcon, Becton-Dickinson, Inc.) for each time point using forceps, and 150 μL of medium containing 10,000 cells are added to each well. The cells are left in the incubator overnight at 37 degrees C. to allow cell attachment to the scaffolds. Media are changed the next day so that half of the wells receive control medium and the other half receive osteogenic induction medium (OS). The media are changed twice a week thereafter.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of preparing an osteoinductive and osteoconductive scaffold to facilitate bone repair, the method comprising the steps:
   (a) preparing a ceramic-polymer solution comprising a bioactive ceramic component comprising from about 10-50% (w/w) of a 20:80 ratio of hydroxyapatite (HA)/tricalcium phosphate (TCP), and a polymer component comprising from about 50-90% (w/w) of polycaprolactone (PCL) dissolved in a solvent selected from the group consisting of methylene chloride (MC), dimethyl formamide (DFM), and a combination thereof; and
   (b) electrospinning the ceramic-polymer solution, and thereby forming a ceramic-polymer composite, and depositing a three-dimensional nonwoven matrix of micron sized electrospun fibers comprising the ceramic-polymer composite on a collector, the three dimensional-nonwoven matrix of electrospun fibers including a plurality of micron sized pores, each micron sized pore of the plurality of micron sized pores having a pore size of at least about 20 microns in diameter.

2. The method according to claim 1, wherein the composite contains at least 10% by weight of the ceramic component.

3. The method according to claim 1, wherein the composite contains at least about 60% by weight of a polymer component.

4. The method according to claim 1, wherein the composite contains at least 10% by weight of the ceramic component and at least about 60% by weight of the polymer component.

5. The method according to claim 1, wherein the polymer component of the composite of step (a) further includes at least one polymer selected from the group consisting of a nondegradable polymer and a degradable polymer.

6. The method according to claim 5, wherein the nondegradable polymer is selected from the group consisting of a polyurethane, a polyvinylidine fluoride, and a polyvinylidine fluoride trifluoroethylene.

7. The method according to claim 5, wherein the degradable polymer is selected from the group consisting of poly(lactic acid-glycolic acid), poly(lactic acid), poly(glycolic acid), a poly(orthoester), a poly(phosphazene), a polyamide, a polysaccharide, and a collagen.

8. The method according to claim 1, further comprising the steps: (c) seeding the three-dimensional nonwoven matrix of electrospun fibers with isolated differentiable human mesenchymal cells or osteoblasts; and (d) growing the differentiable human mesenchymal cells or osteoblasts on the three-dimensional nonwoven matrix of electrospun fibers so that the differentiable human mesenchymal cells or osteoblasts differentiate into a mature cell phenotype on the scaffold.

9. The method according to claim 1, wherein the electrospun fibers in the matrix are characterized by a mean fiber diameter of at least about 20 microns.

10. The method according to claim 1, wherein the electrospun fibers in the matrix are characterized by a mean inter-fiber distance of at least about 90 microns.

11. The method according to claim 1, wherein the micron sized pores are characterized by a mean pore size of at least 80 microns.

12. The method according to claim 1, wherein step (b) includes electrospinning the ceramic-polymer solution at a rate of about 0.1 ml/min at an electrostatic potential of 17 kV, and at a collector-to-needle distance of 15 cm.

* * * * *